United States Patent [19]

Miller et al.

[11] Patent Number: 5,693,661

[45] Date of Patent: Dec. 2, 1997

[54] ANTI-VIRAL COMPOUNDS

[75] Inventors: Shawn C. Miller; Frantz Victor; Wayne A. Spitzer, all of Indianapolis; Thomas R. Sattelberg, Sr., Bloomington; Mark J. Tebbe, Indianapolis, all of Ind.

[73] Assignee: Eli Lilly and Company, Indianapolis, Ind.

[21] Appl. No.: 483,651

[22] Filed: Jun. 7, 1995

[51] Int. Cl.$^6$ .................... A61K 31/415; A61K 31/535; C07D 413/04; C07D 417/04

[52] U.S. Cl. .......... 514/388; 514/63; 514/226.8; 514/234.5; 514/322; 514/363; 514/365; 514/394; 514/395; 548/110; 548/137; 548/181; 548/304.7; 548/306.1; 548/307.4; 548/307.7; 548/308.1; 548/308.4; 548/308.7; 548/309.1; 548/309.7; 548/310.1; 544/53; 544/139

[58] Field of Search ................... 514/63, 226.8, 514/234.5, 322, 363, 365, 388, 394, 395; 548/110, 137, 181, 304.7, 306.1, 307.4, 307.7, 308.1, 308.4, 308.7, 309.1, 309.7, 310.1; 544/53, 139; 546/199

[56] References Cited

U.S. PATENT DOCUMENTS

| | | | |
|---|---|---|---|
| 4,174,454 | 11/1979 | Paget et al. | 548/307.7 |
| 4,420,479 | 12/1983 | Morwick et al. | 548/307.4 |
| 4,492,708 | 1/1985 | Spitzer | 424/273 B |

*Primary Examiner*—Patricia L. Morris
*Attorney, Agent, or Firm*—Janet T. McClain; David E. Boone

[57] ABSTRACT

Certain vinyl acetylene benzimidazole compounds which inhibit the growth of picornaviruses, such as rhinoviruses, enteroviruses, cardioviruses, polioviruses, coxsackieviruses of the A and B groups, echo virus and Mengo virus.

31 Claims, No Drawings

ANTI-VIRAL COMPOUNDS

BACKGROUND OF THE INVENTION

The incidence of viral upper respiratory disease, the common cold, is immense. It has been estimated that nearly a billion cases annually appear in the United States alone. Rhinovirus, a member of the picornaviridae family, is the major cause of the common cold in humans. Because more than 110 strains of rhinoviruses have been identified, the development of a practical rhinovirus vaccine is not feasible, and chemotherapy appears to be the more desirable approach. Another member of the picornavirus family is the enterovirus, which includes approximately eighty human pathogens. Many of these enteroviruses cause cold-like symptoms; others can cause more serious diseases such as polio, conjunctivitis, aseptic meningitus and myocarditus.

Illness related to rhinovirus infection is evidenced by nasal discharge and obstruction. Furthermore, it has been implicated in otitis media, predisposes the development of bronchitis, exacerbates sinusiris, and has been implicated in the precipitation of asthmatic altoclis. Although it is considered by many to be a mere nuisance, its frequent occurrence in otherwise healthy individuals and the resulting economic importance in terms of employee absenteeism and physician visits have made it the subject of extensive investigation.

The ability of chemical compounds to suppress the growth of viruses in vitro may be readily demonstrated using a virus plaque suppression test or a cytopathic effect test (CPE). Cf *Siminoff*, Applied Microbiology, 9(1), 66 (1961). Although a number of chemical compounds that inhibit picornaviruses such as rhinoviruses have been identified, many are unacceptable due to 1) limited spectrum of activity, 2) undesirable side effects or 3) inability to prevent infection or illness in animals or humans. See Textbook of *Human Virology*, edited by Robert B. Belshe, chapter 16, "Rhinoviruses," Roland A. Levandowski, 391–405 (1985). Thus, despite the recognized therapeutic potential associated with a rhinovirus inhibitor and the research efforts expended thus far, a viable therapeutic agent has not yet emerged. For example, antiviral benzimidazole compounds have been disclosed in U.S. Pat. Ser. Nos. 4,008,243, 4,018,790, 4,118,573, 4,118,742 and 4,174,454.

Accordingly, it is a primary object of this invention to provide novel vinyl acetylene benzimidazole compounds which inhibit the growth of picornaviruses, such as rhinoviruses (bovine and human), enteroviruses such as polioviruses, coxsackieviruses of the A and B groups, or echo virus, cardioviruses such as encephalomyocarditis virus (EMC), and apthoviruses such as foot and mouth disease virus.

SUMMARY OF THE INVENTION

The present invention provides compounds of formula I

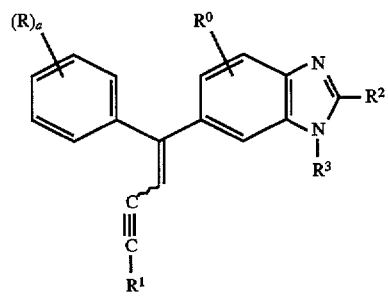

wherein:
a is 1, 2, 3, 4 or 5;
each R is independently hydrogen, hydroxy, thiol, halo, cyano, cyano($C_1$–$C_4$)alkyl, halo($C_1$–$C_4$)alkyl, nitro, amino, $C_1$–$C_4$ alkylamino, di($C_1$–$C_4$)alkylamino, azido, carboxy, $C_1$–$C_6$ alkyl, $C_2$–$C_6$ alkenyl, carbamoyl, carbamoyloxy, carbamoylamino, N-($C_1$–$C_4$)alkylcarbamoyl, —$OCF_3$, —$OCCl_3$, N,N-di($C_1$–$C_4$)alkylcarbamoyl, $C_1$–$C_4$ alkoxy, $C_1$–$C_4$ alkoxycarbonyl, $C_1$–$C_4$ alkoxycarbonyloxy, $C_1$–$C_4$ alkoxycarbonylamino, formyl, $C_2$–$C_4$ alkanoyl, formyloxy, $C_2$–$C_4$ alkanoyloxy, formylamino, $C_2$–$C_4$ alkanoylamino, $C_1$–$C_4$ alkylthio, $C_1$–$C_4$ alkylsulfinyl or $C_1$–$C_4$ alkylsulfonyl;
$R^0$ is hydrogen, halo, $C_1$–$C_4$ alkyl or $C_1$–$C_4$ alkoxy;
$R^1$ is hydrogen, methyl or trimethylsilyl;
$R^2$ is hydrogen, amino, —NHC(O)($C_1$–$C_6$ alkyl) or —$NHSO_2$($C_1$–$C_6$ alkyl);
$R^3$ is $C_1$–$C_6$ alkyl, phenyl, substituted phenyl, furyl, thienyl, thiazol-2-yl, 2-acetamido-4-methyl-thiazol-5-yl, 1,3,4-thiadiazol-2-yl, 2-methyl-1,3,4-thiadiazol-5-yl, 2-methylamino-1,3,4-thiadiazol-5-yl, —$NR^5R^6$, —$SO_2$—$R^4$ or a group of the formula:

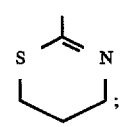

$R^4$ is dimethylamino, $C_1$–$C_6$ alkyl, halo ($C_1$–$C_6$)alkyl, $C_3$–$C_7$ cycloalkyl, phenyl, substituted phenyl or trifluoromethyl; and
$R^5$ and $R^6$ are taken together with the nitrogen atom to which they are attached to form pyrrolidino, piperidino or morpholino;
or a pharmaceutically acceptable salt thereof.

The present invention also provides pharmaceutical formulations comprising a compound of the present invention, or a pharmaceutically acceptable salt thereof, in combination with a pharmaceutically acceptable carrier, diluent or excipient therefor.

The present invention also provides a method for inhibiting a picornavirus comprising administering to a host in need thereof, an effective amount of a compound of formula I, or a pharmaceutically acceptable salt thereof, wherein a, R, $R^0$, $R^1$, $R^2$ and $R^3$ are as defined above.

DETAILED DESCRIPTION OF THE INVENTION

The present invention relates to vinyl acetylene benzimidazole compounds of formula I, as described above, that are useful as antiviral agents.

All temperatures stated herein are in degrees Celsius (°C.). All units of measurement employed herein are in weight units except for liquids which are in volume units.

As used herein, the term "$C_1$–$C_6$ alkyl" represents a straight or branched alkyl chain having from one to six carbon atoms. Typical $C_1$–$C_6$ alkyl groups include methyl, ethyl, propyl, isopropyl, butyl, isobutyl, sec-butyl, t-butyl, pentyl, neo-pentyl, hexyl and the like. The term "$C_1$–$C_6$ alkyl" includes within its definition the term "$C_1$–$C_4$ alkyl."

The term "$C_2$–$C_6$ alkenyl" represents a straight or branched alkenyl chain having from two to six carbon atoms. Typical $C_2$–$C_6$ alkenyl groups include ethenyl, prop-1-enyl, isopropenyl, but-2-enyl, isobut-1-enyl, sec-but-2-enyl, pent-4-enyl, pent-1-enyl, hex-3-enyl and the like.

"Halo" represents chloro, fluoro, bromo or iodo.

"Halo($C_1$–$C_4$)alkyl" represents a straight or branched alkyl chain having from one to four carbon atoms with 1, 2 or 3 halogen atoms attached to it. Typical halo($C_1$–$C_4$)alkyl groups include chloromethyl, 2-bromoethyl, 1-chloroisopropyl, 3-fluoropropyl, 3-bromobutyl, 3-chloroisobutyl, iodo-t-butyl, trichloromethyl, trifluoromethyl, 2,2-chloro-iodoethyl, 2,3-dibromopropyl dichloromethyl and the like.

"Cyano($C_1$–$C_4$)alkyl" represents a straight or branched alkyl chain having from one to four carbon atoms with a cyano moiety attached to it. Typical cyano($C_1$–$C_4$)alkyl groups include cyanomethyl, cyanomethyl, 2-cyanoethyl, 1-cyanoisopropyl, 3-cyanopropyl, 3-cyanobutyl, cyano-t-butyl and the like.

"$C_1$–$C_4$ alkylthio" represents a straight or branched alkyl chain having from one to four carbon atoms attached to a sulfur atom. Typical $C_1$–$C_4$ alkylthio groups include methylthio, ethylthio, propylthio, isopropylthio, butylthio and the like.

"$C_1$–$C_4$ alkoxy" represents a straight or branched alkyl chain having from one to four carbon atoms attached to an oxygen atom. Typical $C_1$–$C_4$ alkoxy groups include methoxy, ethoxy, propoxy, isopropoxy, butoxy and the like.

"$C_1$–$C_4$ alkoxycarbonyl" represents a straight or branched alkoxy chain having from one to four carbon atoms attached to a carbonyl moiety. Typical $C_1$–$C_4$ alkoxy-carbonyl groups include methoxycarbonyl, ethoxycarbonyl, propoxycarbonyl, isopropoxycarbonyl, butoxycarbonyl and the like.

"$C_1$–$C_4$ alkoxycarbonyloxy" represents a straight or branched alkoxy chain having from one to four carbon atoms attached to a carbonyloxy moiety. Typical $C_1$–$C_4$ alkoxycarbonyloxy groups include methoxycarbonyloxy, ethoxycarbonyloxy, propoxycarbonyloxy, isopropoxycarbonyloxy, butoxycarbonyloxy and the like.

"$C_1$–$C_4$ alkoxycarbonylamino" represents a straight or branched alkoxy chain having from one to four carbon atoms attached to a carbonylamino moiety. Typical $C_1$–$C_4$ alkoxycarbonylamino groups include methoxycarbonylamino, ethoxycarbonylamino, propoxycarbonylamino, isopropoxycarbonylamino, butoxycarbonylamino and the like.

"$C_1$–$C_4$ alkylamino" represents a straight or branched alkyl chain having from one to four carbon atoms attached to an amino group. Typical $C_1$–$C_4$ alkylamino groups include methylamino, ethylamino, propylamino, isopropylamino, butylamino, sec-butylamino and the like.

"Di($C_1$–$C_4$)alkylamino" represents two straight or branched alkyl chains having from one to four carbon atoms attached to a common amino group. Typical di($C_1$–$C_4$)alkylamino groups include dimethylamino, ethylmethylamino, methylpropylamino, ethylisopropylamino, butylmethylamino, sec-butylethylamino and the like.

"N-($C_1$–$C_4$)alkylcarbamoyl" represents a straight or branched alkyl chain having from one to four carbon atoms attached to the nitrogen atom of a carbamoyl moiety. Typical N-($C_1$–$C_4$)alkylcarbamoyl groups include N-methylcarbamoyl, N-ethylcarbamoyl, N-propylcarbamoyl, N-isopropylcarbamoyl, N-butylcarbamoyl and N-t-butylcarbamoyl and the like.

"$C_2$–$C_4$ alkanoyl" represents a represents a straight or branched alkyl chain having from one to three carbon atoms attached to a carbonyl moiety. Typical $C_2$–$C_4$ alkanoyl groups include ethanoyl, propanoyl, isopropanoyl, butanoyl and the like.

"$C_2$–$C_4$ alkanoyloxy" represents a straight or branched alkyl chain having from one to three carbon atoms attached to a carbonyloxy moiety. Typical $C_2$–$C_4$ alkanoyloxy groups include ethanoyloxy, propanoyloxy, isopropanoyloxy, butanoyloxy and the like.

"$C_2$–$C_4$ alkanoylamino" represents a straight or branched alkyl chain having from one to three carbon atoms attached to a carbonylamino group. Typical $C_2$–$C_4$ alkanoylamino groups include ethanoylamino, propanoylamino, isopropanoylamino, butanoylamino and the like.

"$C_1$–$C_4$ alkylsulfinyl" represents a straight or branched alkyl chain having from one to four carbon atoms attached to a sulfinyl moiety. Typical $C_1$–$C_4$ alkylsulfinyl groups include methylsulfinyl, ethylsulfinyl, propylsulfinyl, isopropylsulfinyl, butylsulfinyl and the like.

"$C_1$–$C_4$ alkylsulfonyl" represents a straight or branched alkyl chain having from one to four carbon atoms attached to a sulfonyl moiety. Typical $C_1$–$C_4$ alkylsulfonyl groups include methylsulfonyl, ethylsulfonyl, propylsulfonyl, isopropylsulfonyl, butylsulfonyl and the like.

"Substituted phenyl" represents a phenyl ring substituted with halo, $C_1$–$C_4$ alkyl, $C_1$–$C_4$ alkoxy or trifluoromethyl.

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino) ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy) benzyloxycarbonyl, isobornyloxycarbonyl, 1-piperidyloxycarbonyl and the like; benzoylmethylsulfonyl, 2-nitrophenylsulfenyl, diphenylphosphine oxide, t-butyldimethylsilyl, triisopropylsilyl, triphenylsilyl, dimethylthexyl and like amino-protecting groups. The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group(s). Preferred amino-protecting groups are t-butyldimethylsilyl and triisopropylsilyl. Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

As mentioned above, the invention includes the pharmaceutically acceptable salts of the compounds defined by formula I. Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napthhalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds of this invention are those compounds of the formula:

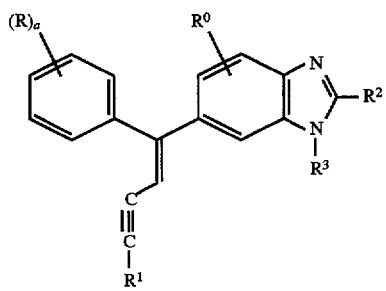

or a pharmaceutically acceptable salt thereof.

Of these preferred compounds, more preferred are those compounds of formula I where:

a is 1, 2 or 3;

each R is independently hydrogen, halo, $C_1$–$C_4$ alkyl, $C_1$–$C_4$ alkoxy, $C_1$–$C_4$ alkylthio, $C_1$–$C_4$ alkylsulfinyl, $C_1$–$C_4$ alkylsulfonyl, trifluoromethyl, di($C_1$–$C_4$) alkylamino or —$OCF_3$;

$R^0$ is hydrogen, halo or $C_1$–$C_4$ alkyl;

$R^1$ is hydrogen;

$R^2$ is amino;

$R^3$ is thiazol-2-yl, phenyl, substituted phenyl or —$SO_2$—$R_4$;

$R_4$ is $C_1$–$C_4$ alkyl, di($C_1$–$C_4$)alkylamino or phenyl; or a pharmaceutically acceptable salt thereof.

Of these compounds, more preferred compounds are those where:

a is 1 or 2;

each R is independently hydrogen, fluoro, methyl, ethyl, methoxy, ethoxy, methylthio, methylsulfinyl, methylsulfonyl or dimethylamino;

$R^0$ is hydrogen;

$R^3$ is thiazol-2-yl, phenyl or —$SO_2$—$R_4$; or a pharmaceutically acceptable salt thereof.

Of these compounds, more preferred compounds are those compounds of the formula:

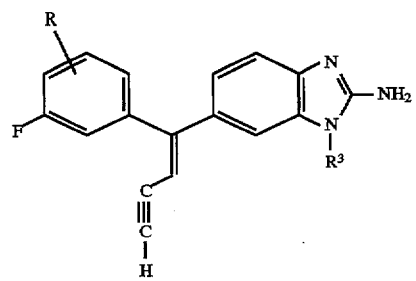

where:

R is independently hydrogen, fluoro, methyl, ethyl, methoxy, ethoxy, methylthio, methylsulfinyl, methylsulfonyl or dimethylamino;

$R^3$ is $-SO_2-CH(CH_3)_2$ or $-SO_2N(CH_3)_2$;

or a pharmaceutically acceptable salt thereof.

Of these compounds, the most preferred compounds are:

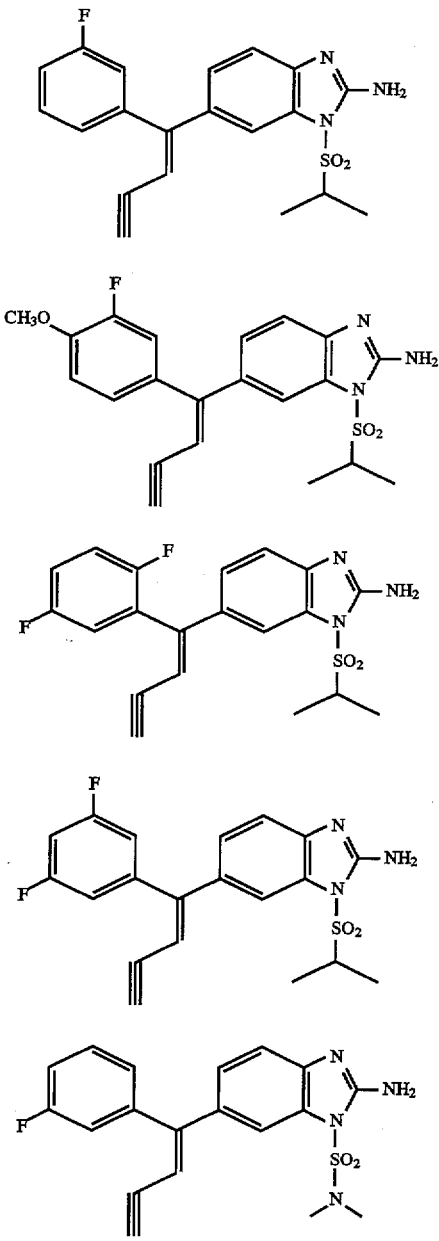

or a pharmaceutically acceptable salt thereof.

The compounds of formula I can be prepared using chemical synthetic methods known in the art. A preferred procedure used to prepare the compounds of formula I involves reacting an appropriately substituted ketone of formula Ia with a suitably substituted Grignard reagent as represented by the following Reaction Scheme I:

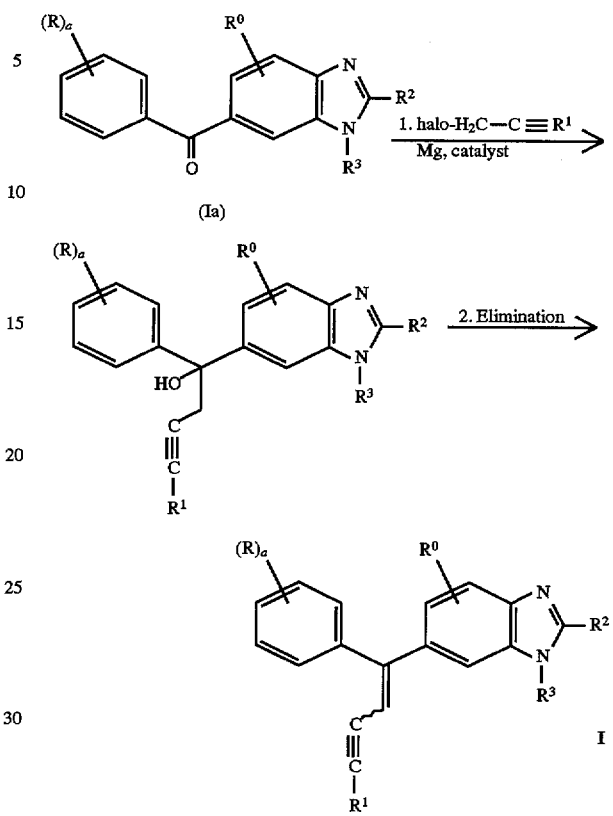

where a, R, $R^0$, $R^1$, $R^2$ and $R^3$ are as defined above.

Reaction Scheme I, above, is accomplished by carrying out reactions 1 and 2. Once a reaction is complete, the intermediate compound may be isolated, if desired, by procedures known in the art. For example, the compound may be crystallized and then collected by filtration, or the reaction solvent may be removed by extraction, evaporation or decantation. The intermediate compound techniques such as crystallization or chromatography over solid supports such as silica gel or alumina, before carrying out the next step of the reaction scheme.

In reaction I.1, the reaction is carried out by combining an appropriately substituted ketone of formula Ia with 3-bromopropyne, preferably 3-bromopropne, in the presence of magnesium and mercury (II) chloride in a mutual inert solvent to provide the corresponding acetylenic alcohol. The 3-halopropyne is generally employed in a substantial molar excess, for example in from a three molar excess to about a ten molar excess relative to the compound of formula Ia, preferably in about a 5 molar excess. Typical solvents suitable for use in this reaction incude any organic solvent such as diethyl ether or tetrahydrofuran. Solvent choice is not critical so long as the solvent employed is inert to the ongoing reaction and the reactants are sufficiently solubilized to effect the desired reaction. The reaction is generally substantially complete after about 1 to 24 hours when conducted at a temperature in the range of from about $-40°$ C. to the the reflux temperature of the reaction mixture. The reaction is preferably conducted under controlled reflux conditions for about 2 to 6 hours. The reaction temperature is generally maintained at a temperature in the range of from about $-5°$ C. to about $66°$ C. The acetylenic alcohol is preferably isolated before being used in reaction I.2.

In reaction I.2, the acetylenic alcohol isolated from reaction I.1 above, is eliminated to provide the vinyl acetylene benzimidazoles of formula I. This reaction may be carried out by sequentially combining the compound prepared in reaction I.1, above, with (1) an acetylene complexing agent, (2) an acid and (3) an oxidizing agent or other agent that is able to remove the complexing agent. A preferred complexing agent is dicobaltoctacarbonyl. Typical acids include p-toluenesulfonic acid, methanesulfonic acid, formic acid, hydrochloric acid, trifluoroacetic acid and the like. Preferred acids are p-toluenesulfonic acid and methanesulfonic acid. A preferred oxidizing agent is ferric nitrate nonahydrate or ceric ammonium nitrate. These reactions are generally carried out using anhydrous organic solvents, under an inert atmosphere such as nitrogen.

Specifically, reaction I.2 is carried out by first combining the acetylenic alcohol with the complexing agent at a temperature in the range of from about 10° C. to about 40° C. for about fifteen minutes to about three hours to provide an acetylene complex. The reaction is generally substantially complete after about forty five minutes to about seventy five minutes when conducted at a temperature in the range of from about 20° C. to 30° C. The complexing agent is generally employed in about equimolar proportions relative to the acetylenic alcohol. Examples of solvents suitable for use in this reaction include diethyl ether, tetrahydrofuran and the like. Solvent choice is not critical so long as the solvent employed is inert to the ongoing reaction and the reactants are sufficiently solubilized to effect the desired reaction. The progress of the reaction may be monitored using thin layer chromatography ("TLC"). When the reaction is substantially complete, the acetylenic alcohol complex is preferably isolated and then combined with an acid in a mutual inert solvent.

The acetylene complex is generally allowed to react with the acid to eliminate the alcohol moiety at a temperature in the range of from about 10° C. to about 40° C. for about twelve hours to about sixty hours to provide a vinyl acetylene complex. For example, reaction with p-toluenesulfonic acid is generally substantially complete after about sixteen hours to about twenty hours when conducted at a temperature in the range of from about 20° C. to 30° C. (methanesulfonic acid requires forty six to fifty hours under the same conditions). The acid reagent is generally employed in an amount ranging from about equimolar proportions to about a one molar excess relative to the acetylenic alcohol complex, preferably in about a 0.25 molar excess. Examples of solvents suitable for use in this reaction include chloroform, methylene chloride, tetrahydrofuran and the like. A preferred solvent is chloroform. Solvent choice is not critical so long as the solvent employed is inert to the ongoing reaction and the reactants are sufficiently solubilized to effect the desired reaction. When the reaction is substantially complete, the excess acid reagent may be removed from the reaction mixture by extraction with water. The vinyl acetylene complex is isolated and then combined with an oxidizing agent in a mutual inert solvent.

The vinyl acetylene complex is generally allowed to react with the oxidizing agent at a temperature in the range of from about 10° C. to about 40° C. for about fifteen minutes to about three hours to provide the vinyl acetylene benzimidazole compounds of formula I. The reaction is generally substantially complete after about forty five minutes to about six hours when conducted at a temperature in the range of from about 20° C. to 30° C. Examples of solvents suitable for use in this reaction include any ethanol or tetrahydrofuran. Solvent choice is not critical so long as the solvent employed is inert to the ongoing reaction and the reactants are sufficiently solubilized to effect the desired reaction. The oxidizing agent is generally employed in an amount ranging from about a two molar excess to about a five molar excess relative to the vinyl acetylene complex, preferably in about a three molar excess. Preferably, the oxidizing agent is added in portions while monitoring the reaction using TLC so that the reaction may be stopped as soon as it is substantially complete. The vinyl acetylene benzimidazole compounds of formula I are preferably isolated and the resulting cis/trans isomers separated using procedures known in the art.

For example, the cis and trans forms of the vinyl acetylene benzimidazole compounds isolated from reaction I.2 may be separated using column chromatography, for example reverse phase HPLC. The compounds may be eluted from the column using an appropriate ratio of acetonitrile and water or methanol and water. The cis form of the compound may be converted to a cis/trans mixture by exposure to hv irradiation and recycled through the above-mentioned purification process.

The acetylenic alcohol compound isolated from reaction I.1 above, may also be eliminated by first reacting the acetylenic alcohol isolated from reaction I.1, above, with a hydrohalic acid, preferably a 3N aqueous solution of hydrochloric acid, to provide a vinyl vinylchloride which is then combined with a base such as an alkali metal alkoxide, preferably potassium t-butoxide to provide the vinyl acetylene benzimidazole compounds of formula I.

In addition, the acetylenic alcohol compound isolated from reaction I.1 above, may be eliminated by activating the hydroxy moiety for elimination in the presence of a base such as tri($C_1$–$C_4$)alkylamine (e.g. triethylamine) or 4-dimethylaminopyridine (DMAP) in an aprotic solvent at a temperature of from about −100° C. to about 40° C. Typical activating agents include methanesulfonylchloride and trifluoromethanesulfonic anhydride. A preferred activating agent is methanesulfonylchloride. The activated compound is eliminated to provide the desired vinyl acetylene by gradually heating the reaction mixture. The activated compound is typically prepared in from about one to eighteen hours when initiated at −78° C. and allowed to progress at room temperature. Examples of solvents suitable for use in this reaction include methylene chloride, chloroform, tetrahydrofuran and the like. Solvent choice is not critical so long as the solvent employed is inert to the ongoing reaction and the reactants are sufficiently solubilized to effect the desired reaction.

The acetylenic alcohol compound where $R^2$ is amino may optionally be protected using an amino protecting group under conditions known in the art. The resultant amino protected acetylenic alcohol compound is then eliminated as described above via an activated compound in the presence of a base in an organic solvent at a temperature of from about −10° C. to about 35° C. Preferred amino protecting groups include t-butyldimethylsilyl and triisopropylsilyl. Preferred bases used with the protected acetylenic alcohol compound include 2,6-lutidine, triethylamine or a combination thereof. A preferred activating agent includes methanesulfonylchloride. The activated compound is typically prepared in from about one to eighteen hours when initiated at 0° C. and allowed to progress at room temperature. Examples of solvents suitable for use in this reaction include methylene chloride, chloroform, tetrahydrofuran and the like.

The compounds of formula I where $R^2$ is —NHC(O)($C_1$–$C_6$ alkyl) or —NHSO$_2$($C_1$–$C_6$ alkyl), may be prepared by acylating or sulfonylating a compound of formula I, where $R^2$ is amino, according to procedures known in the art. For example, the amine compound may be acylated with a suitable acyl halide, isocyanate or chloroformate, preferably in the presence of an acid scavenger such as a tertiary amine, preferably triethylamine. A preferred acylating agent is acetic anhydride. The reaction is typically carried out at a temperature of from about −20° C. to about 25° C. Typical solvents for this reaction include ethers and chlorinated hydrocarbons, preferably diethylether, chloroform or methylene chloride. The amine may be sulfonylated by reaction with a suitably substituted sulfonylating agent in an aprotic solvent. Typical sulfonylating agents include appropriately substituted sulfonyl halides or sulfonic acid anhydrides. A preferred sulfonylating agent is the sulfonyl chloride of the formula ($C_1$-$C_6$ alkyl)-$SO_2$—$C_1$ The reaction is typically carried out at a temperature from about −30° C. to about 50° C. in an aprotic solvent such as tetrahydrofuran or methylene chloride. The amine reactant is generally employed in equimolar proportions relative to the acylating or sulfonylating reactant, and preferably in the presence of equimolar quantities of an acid scavenger such as a tertiary amine. A preferred acid scavenger for this reaction is N-methylmorpholine (NMM) or pyridine. Alternatively, the compound of formula I may be prepared using a ketone of formula Ia that has been acylated or sulfonylated using this procedure.

The compounds of formula I where $R^1$ is trimethylsilyl may be prepared by reacting an appropriately substituted ketone of formula Ia with a Horner-Emmons reagent of the formula $R^1$—$CCCH_2$—$P(O)(OR)_2$ in the presence of a base. The reaction is typically carried out at a temperature of from about −70° C. to about room temperature in an organic solvent such as tetrahydrofuran for one to five hours. Examples of bases include lithium trimethylsilanolate (LiOTMS), lithium bis(trimethylsilyl)amide (LHMDS), pyridine and the like. A preferred base is LHMDS.

The ketone compound of the formula Ia:

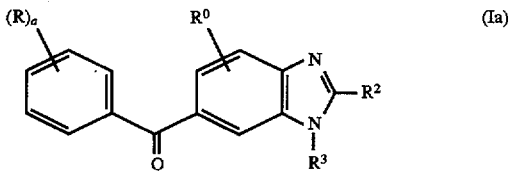

where a, R, $R^0$, $R^2$ and $R^3$ are as defined above, used in Reaction I.1, above, may be prepared according to procedures detailed in the art. For example, the ketone compounds may be prepared substantially as described in Paget et al., U.S. Pat. No. 4,118,742, herein incorporated by reference. In general, Paget et al. describes the preparation of such ketone compounds by ring closing a 3,4-diaminobenzophenone followed by reaction with a sulfonyl halide to provide the desired compounds.

The compounds of formula I may be prepared according to the following Reaction Scheme II.

Reaction Scheme II

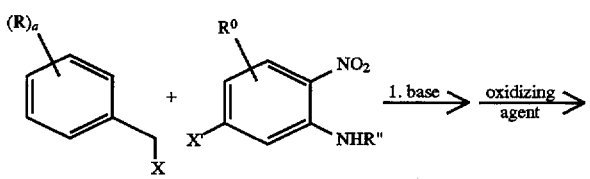

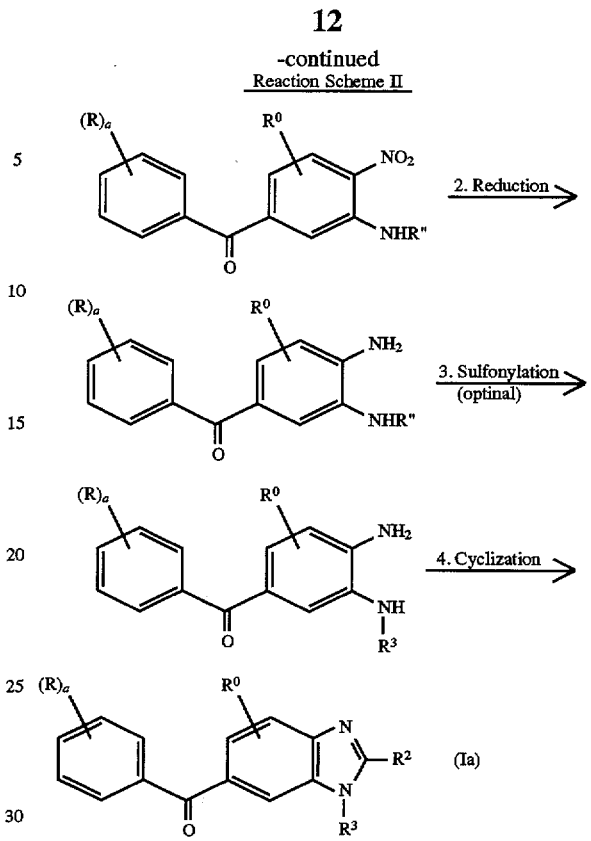

where:

X is cyano or —COOR', where R' is $C_1$-$C_4$ alkyl;

X' is halo;

R" is hydrogen, $C_1$-$C_6$ alkyl, phenyl or substituted phenyl; and a, R, $R^0$, $R^2$ and $R^3$ are defined above.

Reaction Scheme I, above, is accomplished by carrying out reactions 1–4. Once a reaction is complete, the intermediate compound may be isolated, if desired, by procedures known in the art. For example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

Reaction II.1 is accomplished by first exposing an appropriately substituted halo-nitroaniline and an appropriately substituted phenylacetonitrile or benzoate to a base in an organic solvent for one to twenty four hours at a temperature of from about −10° C. to about 40° C. to provide a ketone precursor. The reaction is typically carried out using equimolar proportions of the reactants in the presence of two equivalents of the base. Typical bases include sodium hydride, potassium t-butoxide, lithium diisopropylamide (LDA). A preferred base is potassium t-butoxide. Examples of solvents suitable for use in this reaction include dimethylformamide, dimethylacetamide and the like. Solvent choice is not critical so long as the solvent employed is inert to the ongoing reaction and the reactants are sufficiently solubilized to effect the desired reaction. The ketone precursor is generally prepared in from about one to fifteen hours when the reaction is initiated at 0° C. and allowed to progress at room temperature. The ketone precursor is preferably oxidized in the same reaction mixture without prior isolation or purification.

In particular, the ketone precursor is reacted with an oxidizing agent for thirty minutes to fifteen hours at a temperature of from about 0° C. to about 30° C. to provide the corresponding ketone compound. Typical oxidizing agents include hydrogen peroxide, oxygen and air. The oxygen and air are typically bubbled through the reaction mixture. A preferred oxidizing agent is hydrogen peroxide, preferably in a 30% solution. The ketone is generally prepared in from about thirty minutes to five hours when the reaction is carried out between 0° C. and room temperature. The reaction is preferably monitored by TLC, for example, to ensure that the reaction goes to completion.

In reaction II.2, the nitro substituent on the ketone is reduced according to procedures known in the art to provide the corresponding diaminobenzophenone compound. For example, the nitro substituent may be reduced by catalytic hydrogenation, for example by combining the ketone isolated from reaction II.1 with hydrogen gas in ethanol or tetrahydrofuran and a catalyst. A preferred catalyst is palladium-on-carbon or Raney nickel. Solvent choice is not critical so long as the solvent employed is inert to the ongoing reaction and the nitro reactant is sufficiently solubilized to effect the desired reaction. The hydrogen gas is typically used at a pressure of up to 60 psi, preferably at or about 30 psi. The reaction is generally substantially complete after about 1 to 24 hours when conducted at a temperature in the range of from about 0° C. to about 40° C. The reaction is preferably conducted at a temperature in the range of from about 20° C. to about 30° C. for about 2 to 5 hours.

In reaction II.3, the diaminobenzophenone compound isolated from reaction II.2 where R" is hydrogen may be sulfonylated with an appropriately substituted sulfonyl halide of the formula $R^4$—$SO_2$-halide substantially in accordance with the procedure detailed above to provide the corresponding sulfonamido benzophenone compounds.

In reaction II.4, the compound isolated from reaction II.3 is cyclized via a nitrile intermediate by first exposing the sulfonamido benzophenone compound to a base in an alcoholic solvent such as isopropanol followed by reaction with cyanogen bromide. Typically, the sulfonamido benzophenone and base are reacted at a temperature of from about 0° C. to about 30° C. A preferred base is sodium hydroxide, preferably added in the form of an aqueous solution (about 1–4<u>M</u>). When the sulfonamido benzophenone is completely dissolved, the resultant solution is combined with cyanogen bromide. The cyanogen bromide is typically added in the form of a solution (3–7<u>M</u> for example in acetonitrile). The reaction is generally complete after one to eighteen hours when the reaction mixture is stirred at room temperature. However, in certain instances the nitrile intermediate will precipitate out of the reaction mixture, usually within ten to twenty minutes of the initiation of the reaction. In order to form the desired ketone, this precipitate is isolated and then refluxed in an alcoholic solvent such as isopropanol for one to four hours to provide the desired ketone compound of formula Ia:

The compounds of the formula:

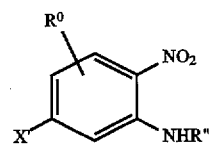

where:
X' and $R^0$ are as defined above; and
R" is $C_1$–$C_6$ alkyl, phenyl or substituted phenyl; used in reaction II.1, above, to prepare compounds of formula I where $R^3$ is $C_1$–$C_6$ alkyl, phenyl or substituted phenyl are prepared by displacing the chloro or fluoro substituent on a compound of the formula

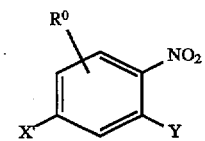

where Y is chloro or fluoro, with the proviso that Y cannot be chloro if X' is fluoro, with a primary amine of the formula $NH_2R^3$, where $R^3$ is $C_1$–$C_6$ alkyl, phenyl or substituted phenyl, in an organic solvent. The reaction is optionally carried out in the presence of an acid scavenger such as potassium carbonate or a large excess of the primary amine. Typical solvents include tetrahydrofuran, dimethylformamide, dimethylacetamide and the like. The reaction is generally complete in one to twenty hours when carried out at a temperature of from about 20° C. to about 80° C. The resultant alkylated halo nitroaniline is then reacted as described in Reaction Scheme II, above.

The compounds employed as initial starting materials in the synthesis of the compounds of this invention are known in the art, and, to the extent not commercially available are readily synthesized by standard procedures commonly employed in the art.

It will be understood by those in the art that in performing the processes described above it may be desirable to introduce chemical protecting groups into the reactants in order to prevent secondary reactions from taking place. Any amine, alcohol alkylamine or carboxy groups which may be present on the reactants may be protected using any standard amino- or carboxy- protecting group which does not adversely affect the remainder of the molecule's ability to react in the manner desired. The various protective groups may then be removed simultaneously or successively using methods known in the art.

The pharmaceutically acceptable salts of the invention are typically formed by reacting a compound of formula I with an equimolar or excess amount of acid or base. The reactants are generally combined in a mutual solvent such as diethyl ether or benzene, for acid addition salts, or water or alcohols for base addition salts. The salts normally precipitate out of solution within about one hour to about ten days and can be isolated by filtration or other conventional methods.

The claimed compounds can occur in either the cis or trans conformation. For the purposes of the present application, cis refers to those compounds where the acetylene moiety is cis to the benzimidazole ring and trans refers to those compounds where the acetylene moiety is trans to the benzimidazole ring. Both isomers are included in the scope of the claimed compounds.

The following Preparations and Examples further illustrate specific aspects of the present invention. It is to be understood, however, that these examples are included for illustrative purposes only and are not intended to limit the scope of the invention in any respect and should not be so construed.

In the following Preparations and Examples, the terms melting point, nuclear magnetic resonance spectra, electron impact mass spectra, field desorption mass spectra, fast atom bombardment mass spectra, infrared spectra, ultraviolet spectra, elemental analysis, high performance liquid chromatography, and thin layer chromatography are abbreviated "m.p.", "NMR", "EIMS", "MS(FD)", "MS(FAB)", "IR", "UV", "Analysis", "HPLC", and "TLC", respectively. The values reported for MS(FD) correspond to mass numbers unless otherwise indicated. In addition, the absorption maxima listed for the IR spectra are only those of interest and not all of the maxima observed.

In conjunction with the NMR spectra, the following abbreviations are used: "s" is singlet, "d" is doublet, "dd" is doublet of doublets, "t" is triplet, "q" is quartet, "m" is multiplet, "dm" is a doublet of multiplets and "br.s", "br.d", "br.t", and "br.m" are broad singlet, doublet, triplet, and multiplet respectively. "J" indicates the coupling constant in Hertz (Hz). Unless otherwise noted, NMR data refers to the free base of the subject compound.

The NMR spectra were obtained on a Brüker Corp. 270 MHz instrument or on a General Electric QE-300 300 MHz instrument. The chemical shifts are expressed in delta values (parts per million downfield from tetramethyl-silane). The MS(FD) spectra were taken on a Varion-MAT 731 Spectrometer using carbon dendrite emitters. EIMS spectra were obtained on a CEC 21-110 instrument from Consolidated Electrodynamics Corporation. IR spectra were obtained on a Perkin-Elmer 281 instrument. UV spectra were obtained on a Cary 118 instrument. TLC was carried out on E. Merck silica gel plates. Melting points are uncorrected.

Preparation 1

A. 3-Amino-4-nitro-4'-fluorobenzophenone

To a cold (0° C.) solution of 17.25 g (100 mmol) of 5-chloro-2-nitroaniline and 12 ml (100 mmol) of 4-fluorophenylacetonitrile in 200 ml of dimethylformamide, was added 22.44 g (200 mmol) of potassium t-butoxide, under nitrogen. The resultant reaction mixture was warmed to room temperature and reacted overnight. When the reaction was substantially complete, as indicated by TLC (eluent of 40% ethyl acetate in hexane), the reaction mixture was cooled to 0° C. followed by the addition of 30 ml of 30% hydrogen peroxide. When the reaction was substantially complete, as indicated by TLC (eluent of 40% ethyl acetate in hexane), the reaction mixture was poured into 1 liter of 1N hydrochloric acid (aqueous) which resulted in the formation of a yellow/orange precipitate. This precipitate was isolated by filtration. Yield: 23.3 g (89%).

B. 3,4-Diamino-4'-fluorobenzophenone

To a solution of 21 g of the subtitled compound of Preparation 1A in 250 ml of tetrahydrofuran and 250 ml of ethanol, was added 3.0 g of Raney Nickel catalyst. The resultant reaction mixture was stirred overnight under 30 psi of hydrogen (gas) and then filtered. The resultant filtrate was concentrated in vacuo to provide a yellow solid which was used without further purification.

C. 4-Amino-3-isopropylsulfonamido-4'-fluorobenzophenone

To a solution of 18.14 g (79 mmol) of the subtitled compound of Preparation 1B in 160 ml of anhydrous methylene chloride and 32 ml of anhydrous pyridine, was added 13.25 ml (118 mmol) of isopropylsulfonylchloride. The resultant reaction mixture was reacted at room temperature for approximately five hours, under nitrogen. When the reaction was substantially complete, as indicated by TLC (eluent of ethyl acetate), the reaction mixture was poured into 400 ml of 1N hydrochloric acid (aqueous). The resulting mixture was diluted with 300 ml of ethyl acetate and the resulting layers were separated, the organic layer was dried over magnesium sulfate, filtered and concentrated in vacuo to provide a dark red gum. This gum was purified using Preparatory HPLC (gradient eluent of 30–60% ethyl acetate in hexane). The fractions containing the desired compound were combined and concentrated in vacuo to provide 17.11 g of a yellow gum that was used without further purification. Yield: 65%

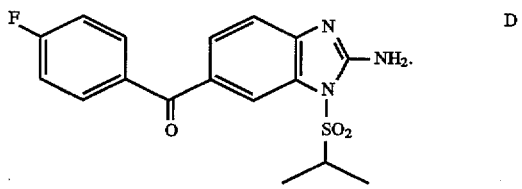

To a solution of 17.11 g (51 mmol) of the subtitled compound of Preparation 1C and 25 ml of 2N sodium hydroxide (aqueous) in 100 ml of isopropanol, was added 10 ml of a 5M cyanogen bromide in acetonitrile. The resultant reaction mixture was reacted at room temperature for approximately thirty minutes resulting in the formation of a precipitate. This precipitate (nitrile intermediate) was isolated by filtration to provide 11.68 g of a solid. This solid was resuspended in 250 ml of isopropanol and the resultant mixture was refluxed until all of the material had dissolved and then cooled to provide 10.0 g of the desired subtitled compound (crystals).

Yield: 55%.

MS (FD): 361.

$^1$H NMR (300 MHz; d$_6$-DMSO): $\delta$1.32 (d, J=7.0 Hz, 6H); 3.96 (septet, J=7.0 Hz, 1H), 7.34–7.44 (m, 5H), 7.63 (dd, J=1.6, 8.3 Hz, 1H), 7.79–7.83 (m, 2H), 7.95 (d, J=1.5 Hz, 1H).

IR (CHCl$_3$): v3081, 1668, 1651, 1600, 1553, 1363, 1285 cm$^{-1}$.

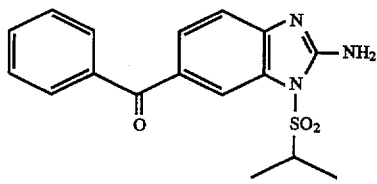

The titled compound was prepared substantially in accordance with the procedure detailed in Preparations 1C–D, using 3,4-diaminobenzophenone.

Analysis for C$_{17}$H$_{17}$N$_3$O$_3$S: Calcd: C, 59.46; H, 4.99; N, 12.24; Found: C, 59.20; H, 5.03; N, 12.03.

Preparation 3

A. 4-Amino-3-isopropylsulfonamido-4'-di(methyl) aminobenzophenone

A solution of 2 g of the subtitled compound of Preparation 1C, 2 g of potassium carbonate and 100 ml of anhydrous dimethylamine was reacted for approximately sixteen hours at 120° C. The reaction mixture was then dried in vacuo to provide a residue. This residue was suspended in a mixture of ethyl acetate and 1N hydrochloric acid (aqueous). The desired subtitled compound was isolated from the organic layer and used without further purificaton.

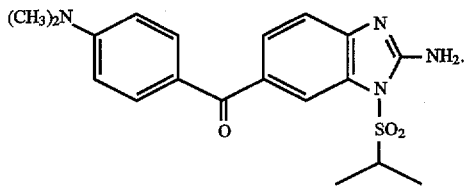

To a cold solution (0° C.) containing 35.64 g (98.6 mmol) of the subtitled compound of Preparation 3A, 400 ml of isopropanol and 50 ml of 2N sodium hydroxide (aqueous), was added 19.8 ml of a 5M cyanogen bromide solution (98.6 mmol). The resultant reaction mixture was warmed to room temperature resulting in the formation of a tan precipitate. This precipitate was isolated by filtration, washed with diethyl ether and then dried in vacuo.

Yield: 28.8 g (76%).

MS (FD): 386.

$^1$H NMR (300 MHz; $d_6$-DMSO): δ1.25 (d, 6H); 3.05 (s, 6H); 3.90 (m, 1H); 6.80 (d, 2H); 7.25–7.85 (m, 7H).

Preparation 4

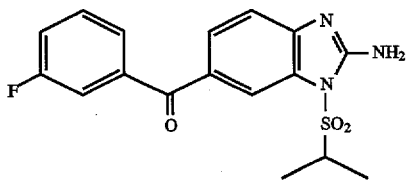

The titled compound was prepared substantially in accordance with the procedure detailed in Preparations 1B–D.

MS(FD): 361.2.

1H NMR (300 MHz; $d_6$-DMSO): δ1.25 (d, 6H); 3.95 (m, 1H); 7.25–7.70 (m, 6H); 7.95 (s, 1H);

IR (CHCl$_3$): v3397, 3016, 1640, 1604, 1588, 1541, 1443, 1387, 1361, 1284, 1271, 1155, 1044, 840 cm$^{-1}$.

EXAMPLE 1

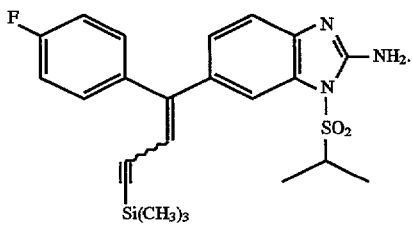

To a cold (−70° C.) solution of 6.21 g (25 mmol) of (3-trimethylsilylprop-2 ynyl)diethoxy phosphonate in 5 ml of anhydrous tetrahydrofuran, was added 30 ml of a 1M solution of lithium bis(trimethylsilyl)amide (LHMDS) in anhydrous tetrahydrofuran (30 mmol). The resultant mixture was stirred for approximately thirty minutes and then was added to a cold (−70° C.) solution of 1.81 g (5 mmol) of subtitled compound of Preparation 1D in 20 ml of tetrahydrofuran. After approximately fifteen minutes, the reaction mixture was warmed to room temperature, reacted overnight and then partitioned between ethyl acetate and an aqueous saturated ammonium chloride solution. The resultant layers were separated and the organic layer was washed with brine, dried over magnesium sulfate, filtered and then dried in vacuo to provide 6.16 g of an oil. This oil was purified using column chromatography (silica gel, gradient eluent of 2–5% methanol in methylene chloride. The fractions containing the desired compound were combined and dried in vacuo to provide 207 mg of (crude) cis isomer and 400 mg of (crude) trans isomer. These crude materials were further purified using radial chromatography (2 mm plate. 5% methanol in methylene chloride) to provide 170 mg of a yellow solid (cis isomer) and 311 mg of a yellow solid (trans isomer).

cis isomer $^1$H NMR (300 MHz; CDCl$_3$): δ0.14 (s, 9H); 1.35 (d, J=7.0 Hz, 6H); 3.58 (septet, J=7.0 Hz, 1H); 5.93 (s, 1H); 6.14 (br.s, 2H); 6.96 (d, J=8.6 Hz, 1H); 6.99 (d, J=8.6 Hz, 1H); 7.22 (dd, J=8.7,5.6 Hz, 2H); 7.35 (dd, J=22.7,8.7 Hz, 2H); 7.64 (s, 1H).

trans isomer $^1$H NMR (300 MHz; CDCl$_3$): δ0.12 (s, 9H); 1.37 (d, J=6.8 Hz, 6H); 3.58 (septet, J=6.8 Hz, 1H); 5.96 (s, 1H); 6.66 (br.s, 2H); 7.00 (d, J=8.6 Hz, 1H); 7.06 (d, J=8.6 Hz, 1H); 7.47 (d, J=10.6 Hz, 2H); 7.48 (dd, J=23.0,8.7 Hz, 2H); 7.53 (d, J=1.2 Hz, 1H).

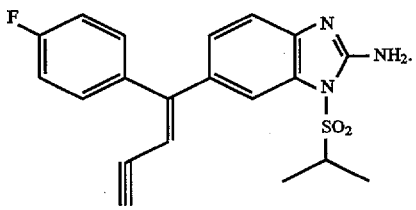

To a solution of 280 mg (0.614 mmol) of the trans isomer isolated from Example 1A in methylene chloride and acetonitrile (1:5), was added 93.3 mg (0.614 mmol) of cesium fluoride. After reacting for approximately two hours at room temperature, the reaction mixture was partitioned between 30 ml of brine and 30 ml of methylene chloride. The resultant layers were separated and the organic layer was dried over sodium sulfate, filtered and then concentrated in vacuo to provide an oil. This oil was purified using revised phase column chromatography (eluent of 0–5% acetonitrile in water) followed by reverse phase HPLC (eluent of 60% acetonitrile in water) to provide 106 mg of the desired subtitled compound.

trans isomer

Yield: 106 mg.

Analysis for $C_{20}H_{18}FN_3O_2S$: Calcd: C, 62.65; H, 4.73; N, 10.96; S, 8.36; F, 4.95; Found: C, 62.43; H, 4.95; N, 10.89; S, 8.06; F, 5.03.

MS(FD): 383.

$^1$H NMR (300 MHz; CDCl$_3$): δ1.40 (d, 6H); 3.05 (s, 1H); 3.63 (m, 1H); 5.98 (s, 1H); 6.45 (s, 2H); 7.00–7.50 (m, 6H); 7.55 (s, 1H).

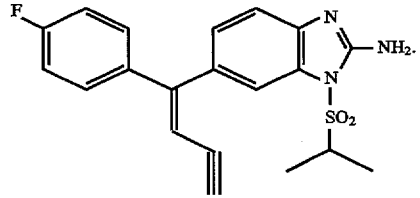

The desired compound was prepared substantially in accordance with the procedure detailed in Example 1B, using 1.91 g (4.19 mmol) of a mixture of cis/trans isomers isolated from Example 1A and 636 mg (4.19 mmol) of cesium fluoride in 50 ml of acetonitrile cis isomer

MS (FD): 383.

¹H NMR (300 MHz; CDCl₃): δ1.43 (d, 6H); 3.00 (s, 1H); 3.71 (m, 1H); 5.98 (s, 1H); 7.00–7.50 (m, 8H); 7.92 (s, 1H).

EXAMPLE 2

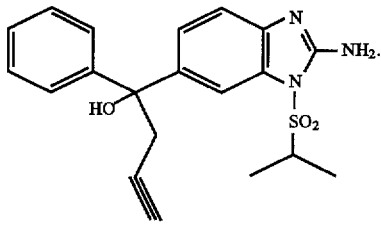

A.

To a refluxing mixture of 30 g (1234 mmol) of magnesium, 500 mg of mercuric chloride and 3 ml of propargyl bromide in 200 ml of anhydrous tetrahydrofuran, was slowly added a mixture of 115 ml of 80% propargyl bromide and 30 g of the titled compound of Preparation 2 in 1200 ml of tetrahydrofuran, under nitrogen. The resultant reaction mixture was reacted for approximately ninety minutes. When the reaction was substantially complete, as indicated by TLC (silica, eluent of 66% of chloroform, 26% ethyl acetate and 8% acetic acid), the reaction mixture was neutralized by the addition of ice and 1N hydrochloric acid and then diluted with 1 liter of ethyl acetate. The resultant layers were separated and the organic layer was dried over magnesium sulfate, filtered and then concentrated in vacuo to provide a residue. This residue was purified using flash chromatography (silica gel, gradient eluent of 0–5% methanol in methylene chloride) to provide 54 g of the desired compound.

Yield: 80%.

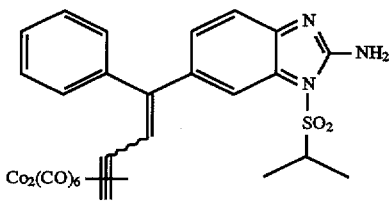

B.

To a solution of 11.4 g (30 mmol) of the subtitled compound of Example 2A in 100 ml of anhydrous tetrahydrofuran, was added 10.2 g (30 mmol) of dicobaltoctacarbonyl, resulting in the formation of a gas. When the reaction was substantially complete, as indicated by TLC, (silica, eluent of 66% chloroform, 26% ethyl acetate and 8% acetic acid), the reaction mixture was concentrated in vacuo to provide a residue. This residue was redissolved in 100 ml of chloroform and reacted with 12 g of p-toluenesulfonic acid for approximately eighteen hours, under nitrogen. The resultant mixture was poured into 1.5 liter of ethyl acetate. The resultant layers were separated and the organic layer was washed with water until the aqueous layer had a pH higher than 5.0. The resultant organic layer containing the desired compound was then dried in vacuo to provide a residue which was used without further purification.

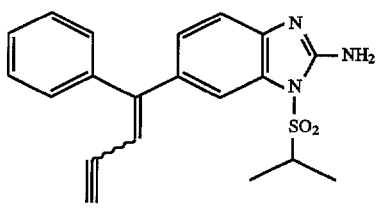

C.

(separation of cis and trans isomers)

To a solution of the subtitled compound of Example 2B in 220 ml of ethanol, was slowly added 50 g of ferric nitrate, under nitrogen. When the reaction was substantially complete, as indicated by TLC, (silica, eluent of 66% chloroform, 26% ethyl acetate and 8% acetic acid), the reaction mixture was diluted with 100 ml of tetrahydrofuran and 1.5 liters of ethyl acetate. The resultant reation mixture was then washed with water, and the organic layer was dried over magnesium sulfate, filtered and concentrated in vacuo to provide a residue. This residue was purified using column chromatography (silica, eluent of 8% acetic acid in methylene chloride) to provide a 1:4 mixture of trans:cis isomers. This mixture was redissolved in 200 ml of methanol and irradiated under UV at 250 nm for 3.5 hours. The reaction was monitored by NFLR and HPLC (55% acetonitrile in water). The reaction was stopped when the isomer ratio was 1:1. The resultant isomers were separated by HPLC (gradient eluent of 50% acetonitrile in water) to provide 300 mg of the trans isomer and 450 mg of the cis isomer.

trans isomer

Analysis for C₂₀H₁₉N₃O₂S: Calcd: C, 65.73; H, 5.24; N, 11.50; S, 8.77; Found: C, 65.52; H, 5.25; N, 11.27; S, 8.74.

MS(FD): 365.

¹H NMR (300 MHz; d₆-DMSO): δ1.22 (d, 6H); 3.86 (m, 1H); 3.95 (s, 1H); 6.16 (s, 1H); 7.10–7.50 (m, 10H).

cis isomer

MS (FD): 365.

¹H NMR (300 MHz; d₆-DMSO): δ1.22 (d, 6H); 3.90 (m, 1H); 4.05 (s, 1H); 6.10 (s, 1H); 7.10–7.50 (m, 9H); 7.70 (s, 1H).

The following compounds were prepared substantially in accordance with the procedure detailed in Example 2A–C, using the appropriately substituted ketone starting material.

EXAMPLE 3

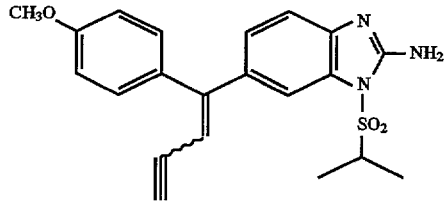

cis isomer

MS (FD): 395.

¹H NMR (300 MHz; CDCl₃): δ1.42 (d, 6H); 2.95 (s, 1H); 3.70 (m, 1H); 3.81 (s, 3H); 5.92 (s, 1H); 6.85 (d, 2H); 7.18–7.40 (m, 6H); 7.85 (s, 1H).

trans isomer

Yield: 310 mg.

MS(FD): 395.

¹H NMR (300 MHz; CDCl₃): δ1.42 (d, 6H); 3.05 (s, 1H); 3.65 (m, 1H); 3.85 (s, 3H); 5.90 (s, 1H); 6.90 (d, 2H); 7.20–7.50 (m, 7H).

EXAMPLE 4

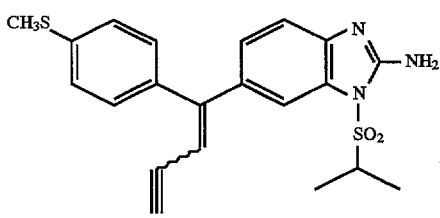

cis isomer

Analysis for $C_{21}H_{21}N_3O_2S_2$: Calcd: C, 61.28; H, 5.14; N, 10.21; Found: C, 60.93; H, 5.27; N, 10.12.

MS(FD): 411.

$^1$H NMR (300 MHz; CDCl$_3$): δ1.42 (d, 6H); 2.52 (s, 3H); 2.97 (s, 1H); 3.70 (m, 1H); 6.00 (s, 1H); 7.10–7.50 (m, 8H); 7.90 (s, 1H).

trans isomer

Yield: 400 mg.

Analysis for $C_{21}H_{21}N_3O_2S_2$: Calcd: C, 61.28; H, 5.14; N, 10.21; Found: C, 60.72; H, 5.20; N, 9.58.

MS(FD): 411.

$^1$H NMR (300 MHz; CDCl$_3$): δ1.45 (d, 6H); 2.52 (s, 3H); 3.12 (s, 1H); 3.70 (m, 1H); 5.95 (s, 1H); 7.20–7.50 (m, 8H); 7.65 (s, 1H).

EXAMPLE 5

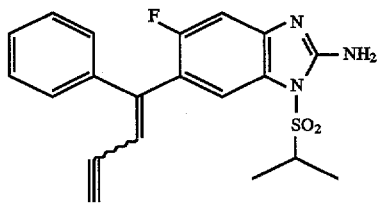

Yield: 3 g of a 1:1 mixture of cis/trans.

MS(FD): 383.

Analysis for $C_{20}H_{18}FN_3O_2S$: Calcd: C, 62.65; H, 4.73; F, 4.95; N, 10.96; S, 8.36; Found: C, 62.37; H, 4.69; F, 5.05; N, 10.73; S, 8.56.

cis isomer $^1$H NMR (300 MHz; CDCl$_3$): δ1.40 (d, 6H); 2.95 (s, 1H); 3.62 (m, 1H); 6.20 (s, 1H); 6.79 (s, 2H); 7.00–7.50 (m, 6H); 7.75 (s, 1H).

trans isomer $^1$H NMR (300 MHz; CDCl$_3$): δ1.40 (d, 6H); 3.10 (s, 1H); 3.62 (m, 1H); 5.95 (s, 1H); 6.70 (s, 2H); 7.00–7.80 (m, 7H).

EXAMPLE 6

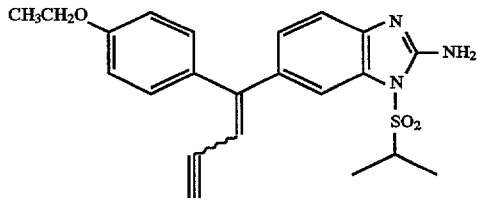

cis isomer

Analysis for $C_{22}H_{23}N_3O_3S$:

MS (FD): 409.

1H NMR (300 MHz; CDCl$_3$): δ1.40 (d, 6H); 1.42 (t, 3H); 2.92 (s, 1H); 3.65 (m, 1H); 4.05 (q, 2H); 5.92 (s, 1H); 6.82 (d, 2H); 7.00–7.40 (m, 6H); 7.85 (s, 1H).

trans isomer

Yield: 325 mg.

Analysis for $C_{22}H_{23}N_3O_3S$:

MS (FD): 409.

$^1$H NMR (300 MHz; CDCl$_3$): δ1.40 (d, 6H); 1.42 (t, 3H); 3.05 (s, 1H); 3.62 (m, 1H); 4.08 (q, 2H); 5.90 (s, 1H); 6.90 (d, 2H); 7.00–7.50 (m, 6H); 7.60 (s, 1H).

EXAMPLE 7

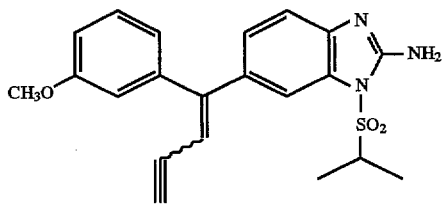

cis isomer

Analysis for $C_{21}H_{21}N_3O_3S$: Calcd: C, 63.78; H, 6.35; N, 10.62; Found: C, 63.06; H, 5.39; N, 10.14.

MS (FD): 395.

$^1$H NMR (300 MHz; CDCl$_3$): δ1.40 (d, 6H); 3.00 s, 1H); 3.65 (m, 1H); 3.79 (s, 3H); 6.05 (s, 1H; 6.80–7.40 (m, 8H); 7.90 (s, 1H).

trans isomer

Yield: 30 mg.

Analysis for $C_{21}H_{21}N_3O_3S$: Calcd: C, 63.78; H, 6.35; N, 10.62; Found: C, 63.05; H, 5.33; N, 10.26.

MS(FD): 395.

$^1$H NMR (300 MHz; CDCl$_3$): δ1.40 (d, 6H); 3.05 (s, 1H); 3.65 (m, 1H); 3.80 (s, 3H); 6.00 (s, 1H); 6.90–7.40 (m, 8H); 7.60 (s, 1H).

EXAMPLE 8

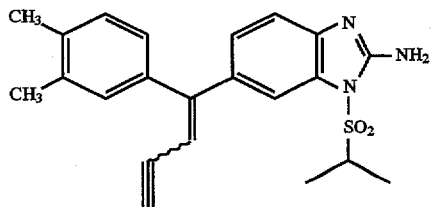

cis isomer

MS (FD): 393.

trans isomer

Yield: 25 mg.

Analysis for $C_{22}H_{23}N_3O_2S$:

MS (FD): 393.

$^1$H NMR (300 MHz; CDCl$_3$): δ1.40 (d, 6H); 2.25 (s, 3H); 2.30 (s, 3H); 3.00 (s, 1H); 3.61 (m, 1H); 5.78 (s, 2H); 5.95 (s, 1H); 7.10–7.20 (m, 5H); 7.60 (d, 1H).

EXAMPLE 9

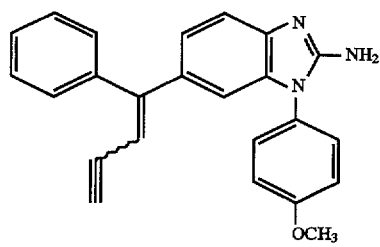

cis isomer

MS(FD): 365.

$^1$H NMR (300 MHz; CDCl$_3$): δ3.00 (s, 3H); 3.83 (s, 3H); 5.14 (s, 2H); 5.90 (s, 1H); 7.00–7.50 (m, 12H).

HPLC (4×300 mm, C18, eluent of 70% acetonitrile in water, 2 ml/min., 254 nm, R$_T$=3.73 minutes).

trans isomer

Yield: 21 mg.

EXAMPLE 10

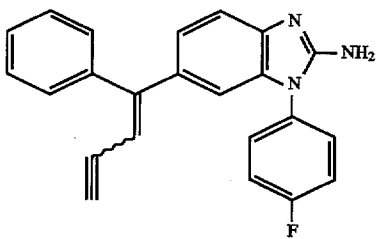

trans isomer

Yield: 680 mg.

Analysis for C$_{23}$H$_{16}$FN$_3$O$_2$S: Calcd: C, 66.18; H, 3.86; N, 10.07; S, 7.68; Found: C, 65.71; H, 3.81; N, 9.84; S, 7.20.

MS (FD): 417.

$^1$H NMR (300 MHz; CDCl$_3$): δ3.03 (s, 1H); 6.00 (s, 1H); 6.30 (s, 2H); 7.20 (m, 9H); 7.52 (s, 1H); 7.88 (m, 2H).

EXAMPLE 11

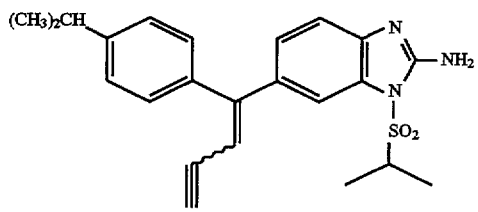

trans isomer

Yield: 30 mg.

MS(FD): 407.

EXAMPLE 12

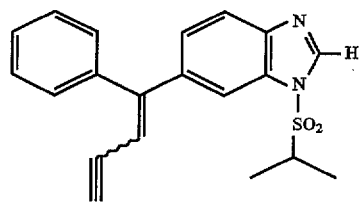

cis isomer

Analysis for C$_{20}$H$_{18}$N$_2$O$_2$S:

MS(FD): 350.

trans isomer

Yield: 200 mg.

Analysis for C$_{20}$H$_{18}$N$_2$O$_2$S: Calcd: C, 68.55; H, 5.18; N, 7.99; S, 9.15; Found: C, 68.70; H, 5.18; N, 7.82; S, 9.17.

MS (FD): 350

$^1$H NMR (300 MHz; CDCl$_3$): δ1.40 (d, 6H); 3.10 (s, 1H); 3.50 (m, 1H); 6.10 (s, 1H); 7.50 (m, 8H); 8.25 (s, 1H).

EXAMPLE 13

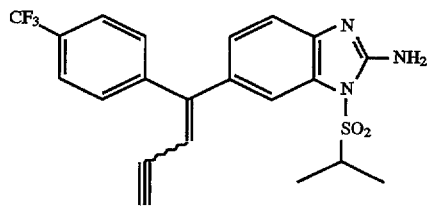

cis isomer

Analysis for C$_{21}$H$_{18}$F$_3$N$_3$O$_2$S:

MS (FD): 433.

$^1$H NMR (300 MHz; CDCl$_3$): δ1.40 (d, 6H); 3.06 (s, 1H); 3.65 (m, 1H); 5.80 (s, 2H); 6.10 (s, 1H); 7.40 (m, 7H).

trans isomer

Yield: 45 mg.

Analysis for C$_{21}$H$_{18}$F$_3$N$_3$O$_2$S: Calcd: C, 58.19; H, 4.19; F, 13.15; N, 9.69; S, 7.40; Found: C, 58.13; H, 4.33; F, 12.91; N, 9.53; S, 7.37.

MS (FD): 433.

$^1$H NMR (300 MHz; CDCl$_3$): δ1.40 (d, 6H); 3.05 (s, 1H); 3.65 (m, 1H); 5.88 (s, 2H); 6.05 (s, 1H); 7.40 (m, 6H); 7.95 (s, 1H).

EXAMPLE 14

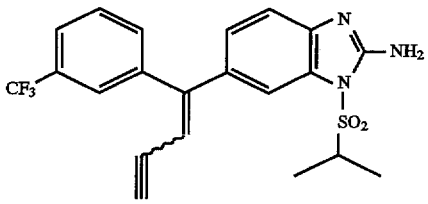

cis isomer

Analysis for C$_{21}$H$_{18}$F$_3$N$_3$O$_2$S: Calcd: C, 58.19; H, 4.19; F, 13.15; N, 9.69; S, 7.40; Found: C, 57.55; H, 4.40; F, 13.96; N, 9.23; S, 7.54.

MS (FD): 433.

¹H NMR (300 MHz; CDCl₃): δ1.40 (d, 6H); 3.04 (s, 1H); 3.65 (m, 1H); 5.80 (s, 2H); 6.02 (s, 1H); 7.40 (m, 6H); 7.85 (s, 1H).

trans isomer

Analysis for C₂₁H₁₈F₃N₃O₂S: Calcd: C, 58.19; H, 4.19; F, 13.15; N, 9.69; S, 7.40; Found: C, 58.04; H, 4.21; F, 13.43; N, 9.40; S, 7.42.

MS (FD): 433.

¹H NMR (300 MHz; CDCl₃): δ1.38 (d, 6H); 3.02 (s, 1H); 3.58 (m, 1H); 5.75 (s, 2H); 6.08 (s, 1H); 7.40 (m, 7H).

EXAMPLE 15

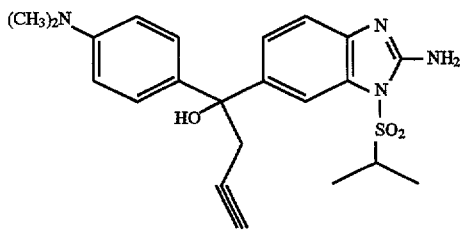

A.

The subtitled compound was prepared substantially as described in Example 2A.

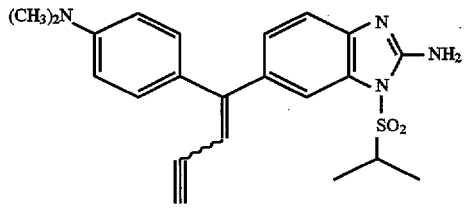

B.

To a solution of 12.8 g (30 mmol) of the subtitled compound of Example 15A in 300 ml of methylene chloride, was added 4.6 ml (39 mmol) of 2,6-lutidine and 8.3 ml (36 mmol) of t-butyldimethylsilyl trifluoromethylsulfonate. After stirring this mixture for approximately one hour, 9.2 g (75 mmol) of 4-dimethylaminopyridine (DMAP) and 19 ml (135 mmol) of triethylamine were added and the resultant mixture was cooled to 0° C., followed by the addition of 8.8 ml (114 mmol) of methanesulfonyl chloride. After approximately five minutes, the reaction mixture was warmed to room temperature and then reacted for approximately two hours. When the reaction was substantially complete, as indicated by TLC, the reaction mixture was diluted with 600 ml of ethyl acetate. The desired compound was extracted from the mixture with a 1N hydrochloric acid solution. The aqueous extracts were combined and basified with a 1N sodium hydroxide solution, and then the desired compound was extracted with ethyl acetate. The resultant organic extracts were combined, dried over magnesium sulfate, filtered and then concentrated in vacuo to provide a reddish solid. This solid was redissolved in 100 ml of acetonitrile and 30 ml of water and cooled, which resulted in the formation of a tan precipitate. This precipitate was isolated by filtration. The filtrate was 2:1 trans/cis. The isomers were separated by Mediem Pressure Liquid Chromatography "MPLC" (gradient eluent of 45–50% acetonitrile in water).

Yield: 6.4 g (89% cis; 8% trans).

cis isomer

Analysis for C₂₂H₂₄N₄O₂S: Calcd: C, 64.68; H, 5.92; N, 13.71; Found: C, 64.38; H, 6.00; N, 13.47.

MS(FD): 408.2.

¹H NMR (300 MHz; d₆-DMSO): δ1.25 (d, 6H); 2.95 (s, 6H); 3.85 (m, 1H); 3.90 (d, 1H); 5.95 (d, 1H); 6.70 (d, 2H); 7.00–7.30 (m, 6H); 7.65 (s, 1H).

trans isomer

Analysis for C₂₂H₂₄N₄O₂S: Calcd: C, 64.68; H, 5.92; N, 13.71; Found: C, 64.47; H, 5.98; N, 13.43.

MS(FD): 408.

¹H NMR (300 MHz; d₆-DMSO): δ1.25 (d, 6H); 2.95 (s, 6H); 3.90 (m, 1H); 3.95 (d, 1H); 5.81 (d, 1H); 6.71 (d, 2H); 7.00–7.40 (m, 7H).

IR (CHCl₃): v3507, 3398, 3306, 1638, 1608, 1584, 1547, 1523, 1439, 1359, 1267, 1155, 1044, 822 cm⁻¹.

EXAMPLE 16

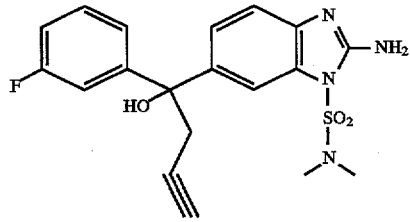

A.

The desired subtitled compound was prepared substantially in accordance with the procedure detailed in Example 2A.

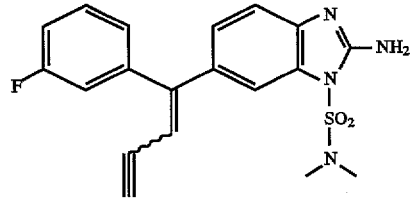

B.

The desired titled compounds were prepared substantially in accordance with the procedure detailed in Example 15, using 11.1 g (27.6 mmol) of the subtitled compound of Example 16A, 4.2 ml (35.9 mmol) of 2,6-lutidine, 7.6 ml (33.1 mmol) of t-butyldimethylsilyl trifluoromethanesulfonate, 8.43 g (69 mmol) of DMAP, 17.3 ml (124 mmol) of triethylamine and 8.1 ml (104.9 mmol) of methanesulfonyl chloride in 300 ml of methylene chloride. The cis and trans isomers were isolated from the resultant crude material using MPLC, (gradient eluent of 38–39% acetonitrile in water).

trans isomer

Analysis for C₁₉H₁₇FN₄O₂S:

MS (FD): 384.

¹H NMR (300 MHz; d₆-DMSO): δ2.80 (s, 6H); 4.05 (d, 1H); 6.20 (d, 1H); 7.05 (br.s, 2H); 7.15–7.30 (m, 6H); 7.50 (m, 1H).

IR (CHCl₃): v3398, 3306, 3019, 2976, 1636, 1610, 1544, 1476, 1442, 1391, 1275, 1170, 1052, 969, 884, 823 cm⁻¹.

EXAMPLE 17

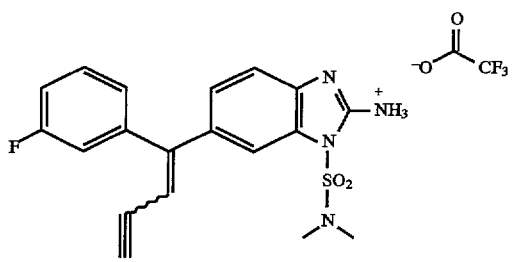

The titled compounds were isolated from the reaction mixture in Example 16.

trans isomer

Analysis for $C_{21}H_{18}F_4N_4O_4S$: Calcd: C, 50.60; H, 3.64; N, 11.24; Found: C, 50.63; H, 3.68; N, 11.01.

MS(FD): 384.

$^1$H NMR (300 MHz; $d_6$-DMSO): δ2.82 (s, 6H); 4.09 (d, 1H); 6.22 (d, 1H); 7.15–7.51 (m, 7H).

IR (CHCl$_3$): ν3441, 3304, 2977, 1690, 1635, 1486, 1441, 1398, 1280, 1195, 1148, 1082, 976, 830 cm$^{-1}$.

EXAMPLE 18

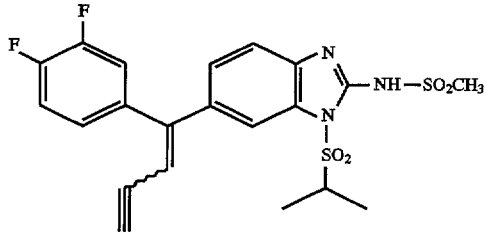

The desired titled compounds were prepared substantially in accordance with the procedure detailed in Example 21.

trans isomer

Analysis for $C_{21}H_{19}F_2N_3O_4S_2$: Calcd: C, 52.60; H, 3.99; N, 8.76; Found: C, 52.49; H, 4.00; N, 8.53.

MS (FD): 479.

$^1$H NMR (300 MHz; CDCl$_3$): δ1.32 (d, J=7 Hz, 6H); 3.08 (s, 3H); 4.17 (d, J=2.6 Hz, 1H); 4.27 (septet, J=6.8 Hz, 1H); 6.23 (d, J=2.6 Hz, 1H); 7.18–7.22 (m, 1H); 7.30 (dd, J=1.5,8.5 Hz, 1H); 7.43 (d, J=8.5 Hz, 1H); 7.40–7.57 (m, 3H).

HPLC (2.6×25 cm, C18, eluent of 50% acetonitrile in water containing 0.1% trifluoroacetic acid, 1.5 ml/min., 254, 320 nm, RT$_T$=12.69 minutes).

cis isomer

HPLC (2.6 mm×25 cm, C18, eluent of 50% acetonitrile in water containing 0.1% trifluoroacetic acid, 1.5 ml/min., 254, 320 nm, R$_T$=14.89 minutes).

EXAMPLE 19

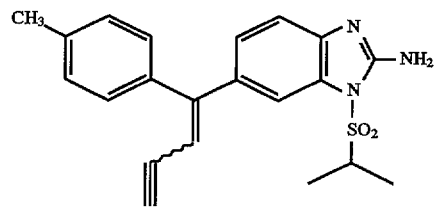

The desired titled compounds were prepared substantially in accordance with the procedure detailed in Example 15.

trans isomer

Analysis for $C_{21}H_{21}N_3O_2S$:

MS (FD): 379.

$^1$H NMR (300 MHz; $d_6$-DMSO): δ1.25 (d, 6H); 2.35 (s, 3H); 3.90 (m, 1H); 3.95 (d, 1H); 6.05 (d, 1H); 7.00–7.40 (m, 9H).

EXAMPLE 20

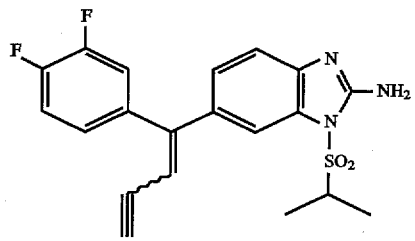

trans isomer

Analysis for $C_{20}H_{17}F_2N_3O_2S$: Calcd: C, 59.84; H, 4.27; N, 10.47; Found: C, 59.86; H, 4.23; N, 10.17.

MS (FD): 401.

$^1$H NMR (300 MHz; $d_6$-DMSO): δ1.24 (d, J=6.6 Hz, 6H); 3.90 (septet, J=6.6 Hz, 1H); 4.10 (d, J=2.6 Hz, 1H); 6.22 (d, J=2.6 Hz, 1H); 7.07–7.12 (m, 3H); 7.18–7.23 (m, 2H); 7.37 (s, 1H); 7.41–7.58 (m, 2H).

IR (CHCl$_3$): ν3398, 3306, 2981, 1639, 1517, 1274, 1043 cm$^{-1}$.

UV/VIS: ν$_{max}$=318.5 nm (E=22343); 261 nm (E=15525), 212.5 nm (E=31019).

HPLC (4.6 mm×25 cm, C18, eluent of 50% acetonitrile in water containing 0.1% trifluoroacetic acid, 1.5 ml/min., 254, 320 nm, R$_T$=5.34 minutes).

cis isomer

HPLC (4.6 mm×25 cm, C18, eluent of 50% acetonitrile in water containing 0.1% trifluoroacetic acid, 1.5 ml/min., 254, 320 nm, R$_T$=5.92 minutes).

EXAMPLE 21

To a cold (−78° C.) solution of 1.60 g (3.99 mmol) of the titled compound of Preparation 4, 1.21 g (9.98 mmol) of DMAP and 2.50 ml (17.96 mmol) of triethylamine in 60.0 ml of methylene chloride, was added 1.17 ml (15.16 mmol) of methanesulfonylchloride. The resultant reaction mixture was slowly warmed to room temperature and reacted overnight. The resultant crude material was purified using reverse phase column chromatography (eluent of 60% acetonitrile in water) followed by HPLC (eluent of 60% acetonitrile in water) to provide 56 mg of trans isomer and 25 mg of cis isomer.

trans isomer

Analysis for $C_{20}H_{18}FN_3O_2S$:

MS(FD): 383.

$^1$H NMR (300 MHz; CDCl$_3$): δ1.38 (d, J=6.9 Hz, 6H); 3.00 (d, J=2.4 Hz, 1H); 3.60 (septet, J=6.8 Hz, 1H); 6.18 (s, 2H); 6.21 (d, J=2.5 Hz, 1H); 7.07–7.27 (m, 4H); 7.35–7.42 (m, 2H); 7.59 (d, J=1.4 Hz, 1H).

Analysis for $C_{20}H_{18}FN_3O_2S$: Calcd: C, 62.65; H, 4.73; N, 10.96; Found: C, 62.92; H, 4.69; N, 10.63.

MS(FD): 383.

$^1$H NMR (300 MHz; CDCl$_3$): δ1.45 (d, J=7.0 Hz, 6H); 3.15 (d, J=2.6 Hz, 1H); 3.72 (septet, J=6.8 Hz, 1H); 5.96 (s, 2H); 6.01 (d, J=2.6 Hz, 1H); 7.03–7.38 (m, 6H); 8.09 (d, J=0.7 Hz, 1H).

The following compounds were prepared substantially in accordance with the procedure detailed in Example 21.

EXAMPLE 22 trans isomer

Analysis for $C_{20}H_{18}FN_3O_2S$:

MS(FD): 383.

IR (CHC$_{13}$): ν3506, 3398, 3306, 1646, 1384, 1087 cm$^{-1}$.

$^1$H NMR (300 MHz; CDCl$_3$): δ1.42 (d, J=6.8 Hz, 6H); 3.11 (d, J=2.6 Hz, 1H); 3.65 (septet, J=6.8 Hz, 1H); 6.01 (d, J=2.6 Hz, 1H); 6.27 (s, 2H); 6.86 (dd, J=6.8, 8.2 Hz, 1H); 7.30–7.39 (m, 4H); 7.50–7.53 (m, 2H).

UV/VIS: λ$_{max}$=287 nm (E=16790); 240 nm (E=37382), 204 nm (E=25933).

HPLC (4.6 mm×25 cm, C18, eluent of 50% acetonitrile in water containing 0.1% trifluoroacetic acid, 1.5 ml/min., 254, 320 nm, R$_T$=10.08 minutes).

cis isomer $^1$H NMR (300 MHz; CDCl$_3$): δ1.45 (d, J=6.9 Hz, 6H); 2.99 (d, J=2.4 Hz, 1H); 3.69 (septet, J=6.9 Hz, 1H); 6.24 (d, J=2.4 Hz, 1H); 6.52 (s, 2H); 7.04 (dd, J=6.4,8.1 Hz, 1H), 7.27–7.39 (m, 5H); 7.42 (d, J=8.4 Hz, 1H).

HPLC (4.6 mm×25 cm, C18, eluent of 50% acetonitrile in water containing 0.1% trifluoroacetic acid, 1.5 ml/min., 254, 320 nm, R$_T$=10.06 minutes).

EXAMPLE 23 trans isomer

HPLC (4.6 mm×25 cm, C18, eluent of 50% acetonitrile in water containing 0.1% trifluoroacetic acid, 1.5 ml/min., 254, 320 nm, R$_T$=4.38 minutes).

cis isomer

HPLC (4.6 mm×25 cm, C18, eluent of 50% acetonitrile in water containing 0.1% trifluoroacetic acid, 1.5 ml/min., 254, 320 nm, R$_T$=4.89 minutes).

EXAMPLE 24 trans isomer m.p. 150°–155° C. (decomp.)

Analysis for $C_{20}H_{18}FN_3O_2S$: Calcd: C, 62.65; H, 4.73; N, 10.96; Found: C, 62.51; H, 4.75; N, 10.77.

MS(FD): 383.

$^1$H NMR (300 MHz; CDCl$_3$): δ1.39 (d, J=6.8 Hz, 6H); 3.05 (d, J=2.4 Hz, 1H); 3.61 (septet, J=6.8 Hz, 1H); 6.02 (d, J=2.4 Hz, 1H); 6.05 (s, 2H); 7.04–7.10 (m, 2H); 7.14–7.39 (m, 4H); 7.55 (s, 1H).

IR (CHCl$_3$): 3506, 3398, 3306, 2999, 1639, 1547, 1442, 1381 cm$^{-1}$.

UV/VIS: λ$_{max}$=317 nm (E=21897); 263 nm (E=15248), 212 nm (E=31161).

HPLC (4.6 mm×25 cm, C18, eluent of 50% acetonitrile in water containing 0.1% trifluoroacetic acid, 1.5 ml/min., 254, 320 nm, R$_T$=4.57 minutes).

cis isomer

HPLC (2.6 mm×25 cm, C18, eluent of 50% acetonitrile in water containing 0.1% trifluoroacetic acid, 1.5 ml/min., 254, 320 nm, R$_T$=5.18 minutes).

EXAMPLE 25 trans isomer m.p. 160°–165° C. (decomp.)

Analysis for $C_{21}H_{20}FN_3O_3S$: Calcd: C, 61.00; H, 4.88; N, 10.16; Found: C, 61.23; H, 4.95; N, 10.44.

$^1$H NMR (300 MHz; CDCl$_3$): δ1.39 (d, J=6.7 Hz, 6H); 3.06 (s, 1H); 3.62 (septet, J=6.8 Hz, 1H); 3.93 (s, 3H); 5.91 (d, J=0.9 Hz, 1H); 6.45 (s, 2H); 6.95 (t, J=8.4 Hz, 1H); 7.09 (d, J=8.2 Hz, 1H); 7.24 (m, 3H); 7.54 (s, 1H).

MS(FD): 413.

IR (CHCl$_3$): 3398, 3306, 2960, 2815, 1638, 1271 cm$^{-1}$.

UV/Vis: $v_{max}$=212.5 nm (E=33257), 272.5 nm E=(17661), 317 nm (E=22342).

HPLC (4.6 mm×25 cm, C18, eluent of 50% acetonitrile in water containing 0.1% trifluoroacetic acid, 1.5 ml/min., 254, 320 nm, R$_T$=4.18 minutes).

cis isomer Analysis for $C_{21}H_{20}FN_3O_3S$: Calcd: C, 61.00; H, 4.88; N, 10.16; Found: C, 60.76; H, 4.79; N, 9.98.

$^1$H NMR (300 MHz; CDCl$_3$): δ1.52 (d, J=6.8 Hz, 6H); 3.00 (d, J=2.3 Hz, 1H); 3.78 (septet, J=6.8 Hz, 1H); 3.93 (s, 3H); 6.01 (d, J=2.3 Hz, 1H); 6.96 (s, 3H); 7.48 (m, 2H); 7.91 (d, J=1.1 Hz, 1H).

MS (FD): 413.

IR (CHCl$_3$): 3400, 3295, 2970, 2830, 1645, 1499 cm$^{-1}$.

UV/ViS: $\lambda_{max}$=213 nm (E=39322), 269.5 nm E=(25418). HPLC (2.6 mm×25 cm, C18, eluent of 50% acetonitrile in water containing 0.1% trifluoroacetic acid, 1.5 ml/min., 254, 320 nm, R$_T$=4.68 minutes).

EXAMPLE 26 trans isomer

Analysis for $C_{20}H_{17}F_2N_3O_2S$: Calcd: C, 59.24; H, 4.27; N, 10.48; Found: C, 59.23; H, 4.27; N, 10.71.

$^1$H NMR (300 MHz; CDCl$_3$): δ1.38 (d, J=6.8 Hz, 6H); 3.05 (d, J=2.5 Hz, 1H); 3.61 (septet, J=6.8 Hz, 1H); 5.93 (s, 2H); 6.21 (d, J=2.5 Hz, 1H); 7.04–7.15 (m, 4H); 7.28 (s, 1H); 7.58 (s, 1H).

MS (FD): 401.

IR (CHC$_{13}$): 3506, 3398, 3307, 2986, 1639, 1493, 1362 cm$^{-1}$.

UV/Vis: $\lambda_{max}$=319.5 (24117), 242.5 (15234), 211 (27698).

HPLC (4.6 mm×25 cm, C18, eluent of 50% acetonitrile in water containing 0.1% trifluoroacetic acid, 1.5 ml/min., 254, 320 nm, R$_T$=4.29 minutes).

cis isomer

HPLC (4.6 mm×25 cm, C18, eluent of 50% acetonitrile in water containing 0.1% trifluoroacetic acid, 1.5 ml/min., 254, 320 nm, R$_T$=5.13 minutes).

EXAMPLE 27 trans isomer $^1$H NMR (300 MHz; d$_6$-DMSO): δ1.25 (d, 6H); 3.90 (m, 1H); 4.06 (d, 1H); 6.22 (d, 1H); 7.05–7.50 (m, 7H).

MS(FD): 399.

EXAMPLE 28 trans isomer

Analysis for $C_{21}H_{18}F_3N_3O_3S$: Calcd: C, 56.12; H, 4.04; N, 9.35; Found: C, 56.17; H, 4.02; N, 9.31.

$^1$H NMR (300 MHz; d$_6$-DMSO): δ1.25 (d, 6H); 3.90 (m, 1H); 4.06 (d, 1H); 6.20 (d, 1H); 7.05–7.55 (m, 7H).

MS(FD): 449.2.

IR (CHCl$_3$): v3398, 3306, 1638, 1547, 1387, 1360, 1262, 1227, 1174, 1044 cm$^{-1}$.

EXAMPLE 29 trans isomer $^1$H NMR (300 MHz; d$_6$-DMSO): δ1.27 (d, J=2.4 Hz, 6H); 3.93 (septet, J=2.4 Hz, 1H); 4.16 (s, 1H); 6.24 (s, 1H); 6.97–7.40 (m, 6H).

MS (FD): 401.1.

IR (CHCl$_3$): v3305.5, 1693.7, 1639.7, 1620.4, 1547.1, 1482.3, 1361.0, 1154.5, 1120.8, 1045.6 cm$^{-1}$.

UV/Vis: λ<sub>max</sub>=: 318 nm (E=15655), 263 nm (E=17393), 213 nm (E=32410).

EXAMPLE 30

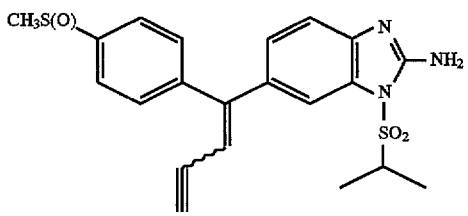

To a solution of 1.2 g (3.11 mmol) of the trans isomer isolated in Example 4 in 150 ml of anhydrous methylene chloride, was added 600 mg (3.11 mmol) of m-chloroperoxybenzoic acid (MCPBA). The resultant reaction mixture was allowed to react overnight. When the reaction was substantially complete, as indicated by TLC, the reaction mixture was washed sequentially with a saturated sodium bicarbonate solution and brine (twice), dried over magnesium sulfate, filtered and then dried in vacuo to provide 1 g of the desired titled compound.

Analysis for $C_{21}H_{21}N_3O_3S_2$:

$^1$H NMR (300 MHz; CDCl$_3$): δ1.40 (d, 6H); 2.80 (s, 3H); 3.05 (s, 1H); 3.61 (m, 1H); 5.95 (s, 2H); 6.05 (s, 1H); 7.40 (m, 7H).

MS(FD): 427.

EXAMPLE 31

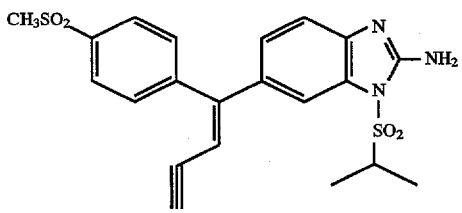

The desired titled compound was prepared substantially in accordance with the procedure detailed in Example 30, using 1.4 g (3.63 mmol) of the trans isomer isolated in Example 4 and 1.75 g of m-chloroperoxybenzoic acid (MCPBA) in 120 ml of anhydrous methylene chloride.

Yield: 1.4 g.

Analysis for $C_{21}H_{21}N_3O_4S_2$:

$^1$H NMR (300 MHz; CDCl$_3$): δ1.40 (d, 6H); 3.05 (s, 1H); 3.15 (s, 3H); 3.61 (m, 1H); 6.01 (s, 2H); 6.15 (s, 1H); 7.05 (d, 1H); 7.17 (s, 1H); 7.58 (s, 1H); 7.65 (d, 2H); 7.98 (d, 2H).

MS(FD): 443.

EXAMPLE 32

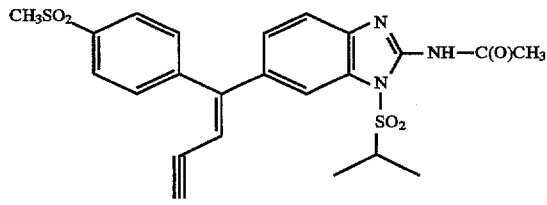

To 100 mg of the trans isomer of Example 2C in 10 ml of acetic anhydride, under nitrogen. The resultant reaction mixture was reacted overnight at room temperature and then poured in ethyl acetate and washed with water (three times). The resultant layers were separated and the organic layer was dried over magnesium sulfate, filtered and then dried in vacuo to provide 60 mg of the desired titled compound.

EXAMPLE 33

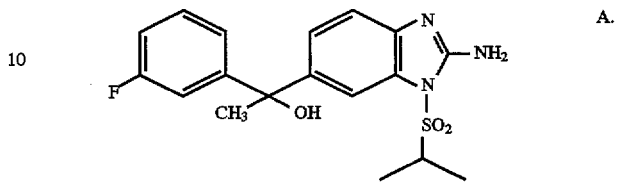

A.

To a cold solution of 25.4 g (70 mmol) of the titled compound of Preparation 4 in 600 ml of anhydrous tetrahydrofuran, was slowly added 117 ml (350 mmol) of methyl magnesiumsbromide. The resultant reaction mixture was reacted while monitoring the temperature in order to keep the temperature below room temperature. When the reaction was substantially complete, as indicated by TLC (approximately one hour), the reaction was quenched by the slow addition of a saturated ammonium chloride solution (aqueous). The resulting layers were separated and the desired compound was extracted from the aqueous layer with ethyl acetate. The resultant organic portions were combined, washed with brine, dried over magnesium sulfate, filtered and concentrated in vacuo to provide 26.4 g of the subtitled compound.

Yield: quantitative.

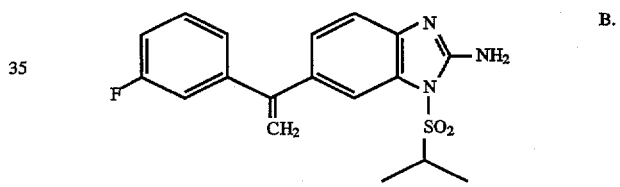

B.

To a solution of 26.4 g (70 mmol) of the subtitled compound of Example 33A in 300 ml of chloroform, was added 27 g of p-toluenesulfonic acid. The resultant reaction mixture was refluxed for approximately two hours. When the reaction was substantially complete, as indicated by TLC, the reaction was cooled to room temperature, washed sequentially with water, a saturated sodium bicarbonate solution and brine, dried over magnesium sulfate, filtered and then concentrated in vacuo to provide a brown foam. This foam was triturated in diethyl ether and then filtered to provide 22.7 g of a tan solid.

Yield: 90%.

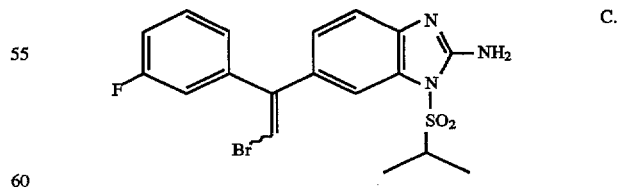

C.

To a solution of 22.6 g (63 mmol) of the subtitled compound of Example 33B in 500 ml of tetrahydrofuran, was added 16.7 g of N-bromosuccinimide. The resultant reaction mixture was refluxed for approximately three hours. When the reaction was substantially complete, as indicated by TLC, the reaction was cooled to room temperature and stirred overnight. The reaction mixture was concentrated in vacuo to provide a residue. This residue was redissolved in 600 ml of ethyl acetate and washed with water, dried over magnesium sulfate, filtered and then concentrated in vacuo to provide a red foam. This foam was dissolved in diethyl ether and then dried in vacuo to provide 32 g of a red solid. The undesirable dibromide compound was separated from the cis/trans bromide mixture by precipitation from acetonitrile to provide 5.66 g of the cis/trans vinyl bromide.

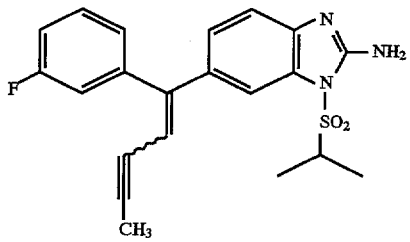

D.

To a solution of 4.00 g (9.1 mmol) of a mixture of the cis/trans compounds of Example 33C in 25 ml of anhydrous tetrahydrofuran, was added 210 mg (0.3 mmol) of bis (triphenylphosphine)palladium (II) chloride, followed by 12.7 ml (91 mmol) of diisopropylamine. After stirring the resultant mixture for approximately ten minutes, 170 mg (0.91 mmol) of copper (I) iodide was added. The resultant mixture was stirred for another ten minutes, and then propyne (gas) was bubbled through the mixture for approximately 1.75 hours. When the reaction was substantially complete, as indicated by TLC, the reaction mixture was diluted with diethyl ether, washed sequentially with a saturated ammonium chloride solution, a 1N hydrochloric acid solution and a saturated sodium bicarbonate solution. The desired compound was extracted from the bicarbonate layer and the resultant organic portions were dried over magnesium sulfate, filtered and then concentrated in vacuo to provide a residue. This residue was purified using flash chromatography (silica; gradient eluent of 60–80% ethyl acetate in hexanes).

Analysis for $C_{21}H_{20}FN_3O_2S$:

trans isomer Calcd: C, 63.46; H, 5.07; N, 10.57; Found: C, 63.24; H, 5.27; N, 10.57.

$^1$H NMR (300 MHz; $d_6$-DMSO): $\delta$1.25 (d, 6H); 1.90 (d, 3H); 3.90 (m, 1H); 6.15 (d, 1H); 7.00–7.50 (m, 9H).

MS(FD): 397.

IR (CHCl$_3$): v3506, 3398, 2984, 1639, 1639, 1610, 1548, 1441, 1360, 1269, 1174, 1155, 1043, 884, 825 cm$^{-1}$.

EXAMPLE 32

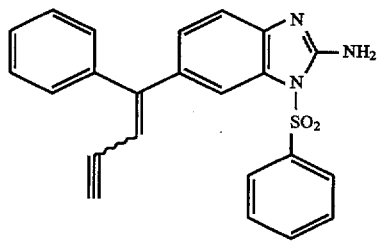

As noted above, the compounds of the present invention are useful as antiviral agents. They have shown inhibitory activity against various strains of enterovirus and rhinovirus. An embodiment of the present invention is a method of treating or preventing picornaviridae infection comprising administering to a host in need thereof an effective amount of a compound of formula I or a pharmaceutically acceptable salt thereof.

The term "effective amount" as used herein, means an amount of a compound of formula I which is capable of inhibiting viral replication. The picornaviridae inhibition contemplated by the present method includes either therapeutic or prophylactic treatment, as appropriate. The specific dose of compound administered according to this invention to obtain therapeutic or prophylactic effects will, of course, be determined by the particular circumstances surrounding the case, including, for example, the compound administered, the route of administration, the condition being treated and the individual being treated. A typical daily dose will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of formula I or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations are prepared by known procedures using well-known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

The following formulation examples are illustrative only and are not intended to limit the scope of the invention in any way. The term "active ingredient" means a compound according to formula I or a pharmaceutically acceptable salt thereof.

Formulation 1

Hard gelatin capsules are prepared using the following ingredients:

|  | Quantity (mg/capsule) |
|---|---|
| Active ingredient | 250 |
| Starch, dried | 200 |

-continued

| | Quantity (mg/capsule) |
|---|---|
| Magnesium stearate | 10 |
| Total | 460 mg |

Formulation 2

A tablet is prepared using the ingredients below:

| | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

| | Weight |
|---|---|
| Active ingredient | 0.25 |
| Methanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| | Quantity (mg/tablet) |
|---|---|
| Active ingredient | 60 |
| Starch | 45 |
| Microcrystalline cellulose | 35 |
| Polyvinylpyrrolidone (as 10% solution in water) | 4 |
| Sodium carboxymethyl starch | 4.5 |
| Magnesium stearate | 0.5 |
| Talc | 1 |
| Total | 150 |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve.

The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| | Quantity (mg/capsule) |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 mL dose, are made as follows:

| Active ingredient | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 mL |

The solution of the above ingredients generally is administered intravenously to a subject at a rate of 1 mL per minute.

The following experiment was carried out to demonstrate the ability of the compounds of formula I to inhibit the test virus.

Test Methods

African green monkey kidney cells (BSC-1) or Hela cells (5-3) were grown in 25 cc Falcon flasks at 37° C. in medium 199 with 5 percent inactivated fetal bovine serum (FBS), penicillin (150 units 1 ml) and streptomycin (150 micrograms per milliliter (µg/ml)). When confluent monolayers were formed, the supernatant growth medium was removed and 0.3 ml of an appropriate dilution of virus (e.g. echo, Mengo, Coxsackie, polio or rhinovirus) were added to each flask. After absorption for one hour at room temperature, the virus infected cell sheet was overlaid with a medium comprising one part of 1 percent Ionagar No. 2 and one part double strength medium 199 with FBS, penicillin and streptomycin which contains drug at concentrations of 100, 50, 25, 12, 6, 3 and 0 µg/ml. The flask containing no drug served as the control for the test. The stock solutions of vinyl acetylene benzimidazole compounds were diluted with dimethylsulfoxide to a concentration of $10^4$ µg/ml. The flasks were then incubated for 72 hours at 37° C. for polio, Coxsackie, echo and Mengo virus and 120 hours at 32° C. for rhinovirus. Virus plaques were seen in those areas were the virus infected and reproduced in the cells. A solution of 10 percent formalin and 2 percent sodium acetate was added to each flask to inactivate the virus and fix the cell sheet to the surface of the flask. The virus plaques, irrespective of size, were counted after staining the surrounding cell areas with crystal violet. The plaque count was compared to the control count at each drug concentration. The activity of the test compound was expressed as percentage plaque reduction, or percent inhibition. Alternatively, the drug concentration which inhibits plaque formation by 50 percent can be used as a measure of activity. The 50 percent inhibition is indicated by the symbol $IC_{50}$.

Test results for various vinyl acetylene benzimidazole compounds are summarized in Tables 1 and 2 by Example number and indicating the test virus and the percent inhibition of plaque reduction which is presented as an $IC_{50}$ value. Such $IC_{50}$ values represent the amount of test compound (µg/ml) that is needed to inhibit 50% of the plaque formation.

TABLE 1

| | IC50 (µg/ml) | | | | |
|---|---|---|---|---|---|
| Example No | PV-1 | RhV-1 | RhV-2 | RhV-14 | RhV-16 |
| 1A (trans) | | | | 10.9 | |
| 1A (cis) | | | | 3.9 | |
| 1B (trans) | | 0.078 | 0.091 | 0.101 | 0.032 |
| 1C (cis) | 6.2 | | | | |
| 2C (trans) | 0.035 | 0.033 | 0.065 | 0.081 | 0.039 |
| 2C (cis) | 0.19 | | | | |
| 3 (trans) | 0.21 | 0.03 | 0.041 | 0.059 | 0.029 |
| 4 (trans) | 0.5 | | | | |
| 5 (trans) | | | | 1.9 | |
| 6 | 0.07 | | | | |
| 7 | 0.08 | | | | |
| 8 (trans) | 0.1 | | | | |
| 9 (trans) | 0.11 | | | | |
| 9 (cis) | 0.52 | | | | |
| 10 (trans) | 0.1 | | | | |
| 10 (cis) | 0.66 | | | | |
| 11 (trans) | 0.088 | | | | |
| 11 (cis) | 2.74 | | | | |
| 12 (trans) | 19.2 | | | | |
| 12 (cis) | 50 | | | | |
| 13 (trans) | 0.12 | | | | |
| 14 (trans) | | | | 0.331 | |
| 15B (trans) | | | | 0.1 | |
| 16B (trans) | | | | 0.038 | |
| 17 (trans) | | | | 0.071 | |
| 18 (trans) | | | | 1.88 | |
| 19 (trans) | | | | 0.078 | |
| 20 (trans) | | | | 0.155 | |
| 21 (trans) | | | | 0.078 | |
| 21 (cis) | | | | 0.478 | |
| 22 (trans) | | | | 1.9 | |
| 23 (trans) | | | | 3.9 | |
| 24 (trans) | | 0.027 | 0.069 | 0.088 | 0.057 |
| 25 (trans) | | 0.049 | 0.054 | 0.065 | 0.06 |
| 25 (cis) | | | | 0.428 | |
| 26 (trans) | | 0.096 | 0.079 | 0.115 | 0.099 |
| 27 (trans) | | 0.129 | 0.123 | 0.253 | 0.185 |
| 28 (trans) | | | 0.535 | | |
| 29 (trans) | | 0.124 | 0.176 | 0.236 | 0.261 |
| 30 (trans) | 0.07 | | | | |
| 31 (trans) | 0.05 | | | | |
| 32 | | | | | |
| 33D (trans) | | | | 0.19 | |
| 34 (trans) | 0.09 | | | | |
| 34 (cis) | 0.17 | | | | |

PV (poliovirus); RhV (Rhinovirus)
the numbers following the virus designation represent particular strains.

TABLE 2

| | IC50 (µg/ml) | | |
|---|---|---|---|
| Example No | CS-A21C | CS-A21M | CS-B3 |
| 1A (trans) | | | |
| 1A (cis) | | | |
| 1B (trans) | 0.062 | 0.062 | |
| 1C (cis) | | | 0.1 |
| 2C (trans) | 0.32 | | |
| 2C (cis) | | | 0.055 |
| 24 (trans) | | | 0.057 |
| 25 (trans) | | | 0.06 |
| 25 (cis) | | | |
| 26 (trans) | | | 0.099 |
| 27 (trans) | | | 0.185 |
| 28 (trans) | | | |
| 29 (trans) | | | 0.261 |

CS (Coxsackie virus)
the numbers following the virus designation represent particular strains

We claim:

1. A compound of the formula I

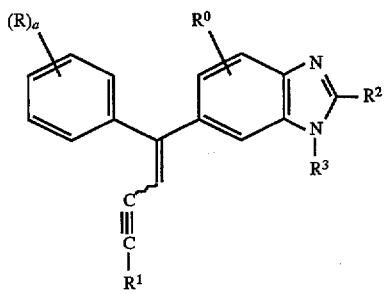

wherein:

a is 1, 2, 3, 4 or 5;

each R is independently hydrogen, hydroxy, thiol, halo, cyano, cyano($C_1$-$C_4$)alkyl, halo($C_1$-$C_4$)alkyl, nitro, amino, $C_1$-$C_4$alkylamino, di($C_1$-$C_4$)alkylamino, azido, carboxy, $C_1$-$C_6$ alkyl, $C_2$-$C_6$ alkenyl, carbamoyl, carbamoyloxy, carbamoylamino, N-($C_1$-$C_4$)alkylcarbamoyl, —$OCF_3$, —$OCCl_3$, N,N-di($C_1$-$C_4$)alkylcarbamoyl, $C_1$-$C_4$ alkoxy, $C_1$-$C_4$ alkoxycarbonyl, $C_1$-$C_4$ alkoxycarbonyloxy, $C_1$-$C_4$ alkoxycarbonylamino, formyl, $C_2$-$C_4$ alkanoyl, formyloxy, $C_2$-$C_4$ alkanoyloxy, formylamino, $C_2$-$C_4$ alkanoylamino, $C_1$-$C_4$ alkylthio, $C_1$-$C_4$ alkylsulfinyl or $C_1$-$C_4$ alkylsulfonyl;

$R^0$ is hydrogen, halo, $C_1$-$C_4$ alkyl or $C_1$-$C_4$ alkoxy;

$R^1$ is hydrogen, methyl or trimethylsilyl;

$R^2$ is hydrogen, amino, —NHC(O)($C_1$-$C_6$ alkyl) or —$NHSO_2$($C_1$-$C_6$ alkyl);

$R^3$ is $C_1$-$C_6$ alkyl, phenyl, phenyl substituted by halogen, $C_1$-$C_4$-alkyl, $C_1$-$C_4$ alkoxy, or trifluoromethyl, furyl, thienyl, thiazol-2-yl, 2-acetamido-4-methyl-thiazol-5-yl, 1,3,4-thiadiazol-2-yl, 2-methyl-1,3,4-thiadiazol-5-yl, 2-methylamino-1,3,4-thiadiazol-5-yl, —$NR^5R^6$, —$SO_2$—$R^4$ or a group of the formula:

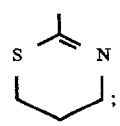

$R^4$ is dimethylamino, $C_1$-$C_6$ alkyl, halo($C_1$-$C_6$)alkyl, $C_3$-$C_7$ cycloalkyl, phenyl, phenyl substituted by halogen, $C_1C_4$ alkyl, $C_4$-alkoxy, or trifluoromethyl; and $R^5$ and $R^6$ are taken together with the nitrogen atom to which they are attached to form pyrrolidino, piperidino or morpholino;

or a pharmaceutically acceptable salt thereof.

2. A compound as claimed in claim 1 of the formula:

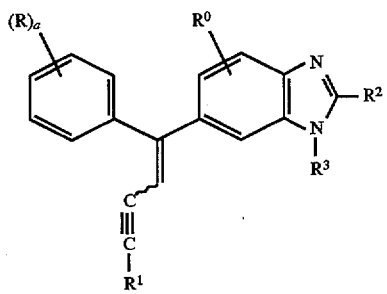

or a pharmaceutically acceptable salt thereof.

3. A compound according to claim 2 where:

a is 1, 2 or 3;

each R is independently hydrogen, halo, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, trifluoromethyl, di($C_1$-$C_4$) alkylamino or —$OCF_3$;

$R^0$ is hydrogen, halo or $C_1$-$C_4$ alkyl;

$R^1$ is hydrogen;

$R^2$ is amino;

$R^3$ is thiazol-2-yl, phenyl, phenyl substituted by halogen, $C_1$-$C_4$ alkyl, $C_1$-$C_4$ alkoxy, trifluoromethyl, or —$SO_2$—$R_4$;

$R_4$ is $C_1$-$C_4$ alkyl, di($C_1$-$C_4$)alkylamino or phenyl; or a pharmaceutically acceptable salt thereof.

4. A compound according to claim 3 where:

a is 1 or 2;

each R is independently hydrogen, fluoro, methyl, ethyl, methoxy, ethoxy, methylthio, methylsulfinyl, methylsulfonyl or dimethylamino;

$R^0$ is hydrogen;

$R^3$ is thiazol-2-yl, phenyl or —$SO_2$—$R_4$;

or a pharmaceutically acceptable salt thereof.

5. A compound according to claim 4 of the formula:

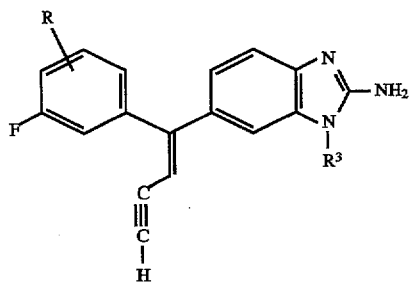

where:

R is independently hydrogen, fluoro, methyl, ethyl, methoxy, ethoxy, methylthio, methylsulfinyl, methylsulfonyl or dimethylamino;

$R^3$ is —$SO_2$—$CH(CH_3)_2$ or —$SO_2$—$NH(CH_3)_2$;

or a pharmaceutically acceptable salt thereof.

6. A compound according to claim 5 which is:

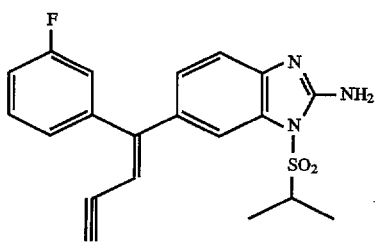

or a pharmaceutically acceptable salt thereof.

7. A compound according to claim 5 where:

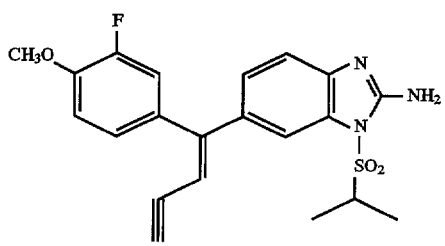

or a pharmaceutically acceptable salt thereof.

8. A compound according to claim 5 where:

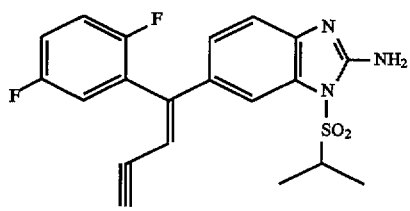

or a pharmaceutically acceptable salt thereof.

9. A compound according to claim 5 where:

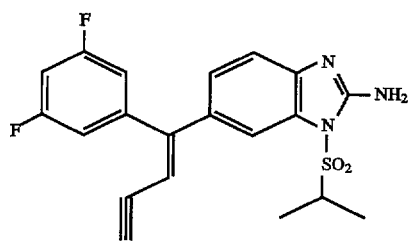

or a pharmaceutically acceptable salt thereof.

10. A compound according to claim 5 where:

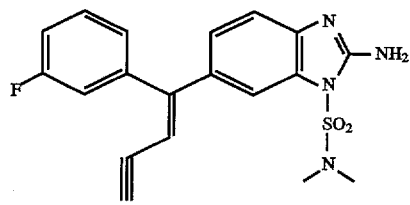

or a pharmaceutically acceptable salt thereof.

11. A pharmaceutical formulation comprising one or more pharmaceutically acceptable carriers, diluents or excipients and a compound of claim 1.

12. A pharmaceutical formulation as claimed in claim 11 where the compound has the formula:

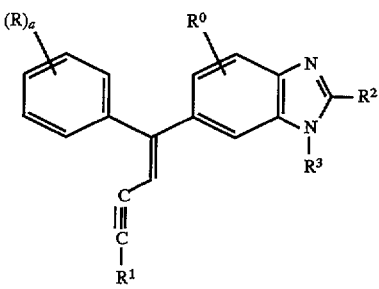

or a pharmaceutically acceptable salt thereof.

13. A pharmaceutical formulation according to claim 12 where the compound is one where:

a is 1, 2 or 3;

each R is independently hydrogen, halo, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, trifluoromethyl, di($C_1$-$C_4$)alkylamino or —$OCF_3$;

$R^0$ is hydrogen, halo or $C_1$-$C_4$ alkyl;

$R^1$ is hydrogen;

$R^2$ is amino;

$^3$ is thiazol-2-yl, phenyl, phenyl substituted by halogen, $C_1$-$C_4$ alkyl, $C_1$-$C_4$ alkoxy, trifluoromethyl, or —$SO_2$—$R_4$; $R_4$ is $C_1$-$C_4$ alkyl, di($C_1$-$C_4$)alkylamino or phenyl; or a pharmaceutically acceptable salt thereof.

14. A pharmaceutical formulation according to claim 13 where the compound is one where:

a is 1 or 2;

each R is independently hydrogen, fluoro, methyl, ethyl, methoxy, ethoxy, methylthio, methylsulfinyl, methylsulfonyl or dimethylamino;

$R^0$ is hydrogen;

$R^3$ is thiazol-2-yl, phenyl or —$SO_2$—$R_4$; or a pharmaceutically acceptable salt thereof.

15. A pharmaceutical formulation according to claim 14 where the compound has the formula:

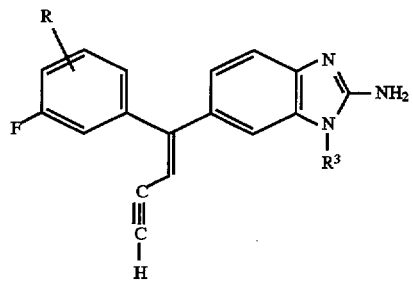

where:

R is independently hydrogen, fluoro, methyl, ethyl, methoxy, ethoxy, methylthio, methylsulfinyl, methylsulfonyl or dimethylamino;

$R^3$ is —$SO_2$—$CH(CH_3)_2$ or —$SO_2$—$NH(CH_3)_2$;

or a pharmaceutically acceptable salt thereof.

16. A pharmaceutical formulation according to claim 15 where the compound is:

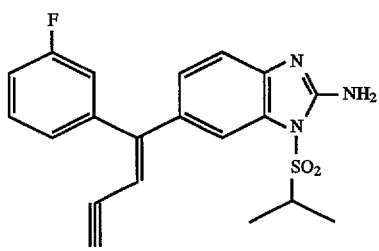

or a pharmaceutically acceptable salt thereof.

17. A pharmaceutical formulation according to claim 15 where the compound is:

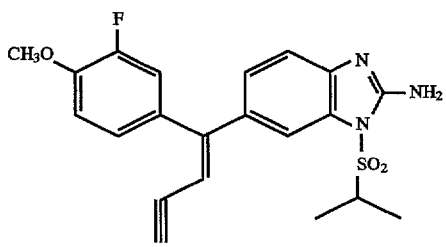

or a pharmaceutically acceptable salt thereof.

18. A pharmaceutical formulation according to claim 15 where the compound is:

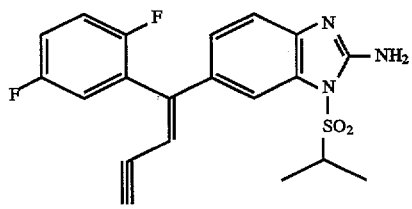

or a pharmaceutically acceptable salt thereof.

19. A pharmaceutical formulation according to claim 15 where the compound is:

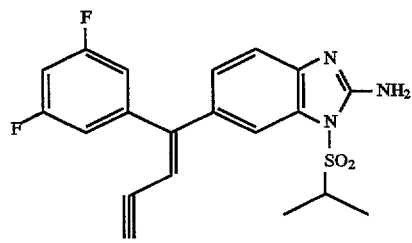

or a pharmaceutically acceptable salt thereof.

20. A pharmaceutical formulation according to claim 15 where the compound is:

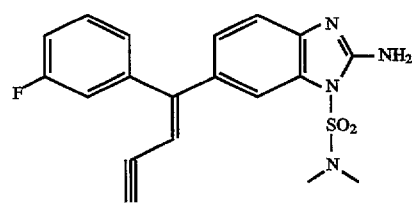

or a pharmaceutically acceptable salt thereof.

21. A method for inhibiting a picornavirus comprising administering to a host in need thereof, an effective amount of a compound of claim 1.

22. A method as claimed in claim 21 where the compound has the formula:

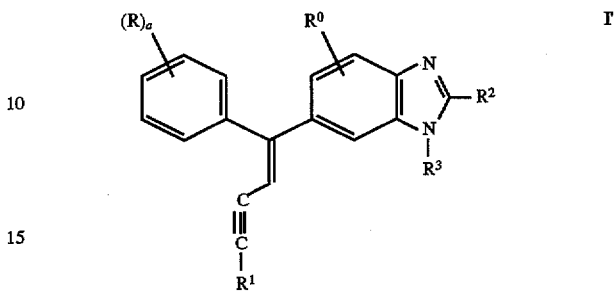

or a pharmaceutically acceptable salt thereof.

23. A method according to claim 22 where the compound is one where:

a is 1, 2 or 3;

each R is independently hydrogen, halo, $C_1$–$C_4$ alkyl, $C_1$–$C_4$ alkoxy, $C_1$–$C_4$ alkylthio, $C_1$–$C_4$ alkylsulfinyl, $C_1$–$C_4$ alkylsulfonyl, trifluoromethyl, di($C_1$–$C_4$) alkylamino or —$OCF_3$;

$R^0$ is hydrogen, halo or $C_1$–$C_4$ alkyl;

$R^1$ is hydrogen;

$R^2$ is amino;

$R^3$ is thiazol-2-yl, phenyl, phenyl substituted by haloaen $C_1$–$C_4$ alkyl, $C_1$–$C_4$ alkoxy, trifluoromethyl, or —$SO_2$—$R_4$;

$R_4$ is $C_1$–$C_4$ alkyl, di($C_1$–$C_4$)alkylamino or phenyl; or a pharmaceutically acceptable salt thereof.

24. A method according to claim 23 where the compound is one where:

a is 1 or 2;

each R is independently hydrogen, fluoro, methyl, ethyl, methoxy, ethoxy, methylthio, methylsulfinyl, methylsulfonyl or dimethylamino;

$R^0$ is hydrogen;

$R^3$ is thiazol-2-yl, phenyl or —$SO_2$—$R_4$;

or a pharmaceutically acceptable salt thereof.

25. A method according to claim 24 where the compound has the formula:

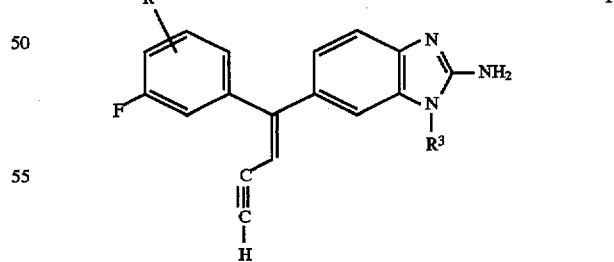

where:

R is independently hydrogen, fluoro, methyl, ethyl, methoxy, ethoxy, methylthio, methylsulfinyl, methylsulfonyl or dimethylamino;

$R^3$ is —$SO_2$—$CH(CH_3)_2$ or —$SO_2$—$NH(CH_3)_2$; or a pharmaceutically acceptable salt thereof.

26. A method according to claim 25 where the compound is:

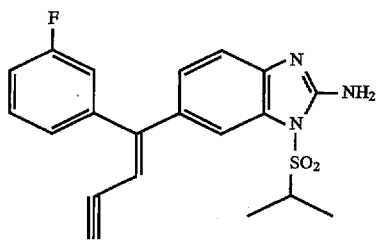

or a pharmaceutically acceptable salt thereof.

27. A method according to claim 25 where the compound is:

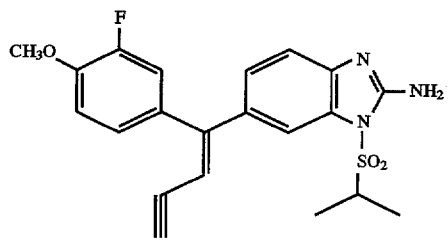

or a pharmaceutically acceptable salt thereof.

28. A method according to claim 25 where the compound is:

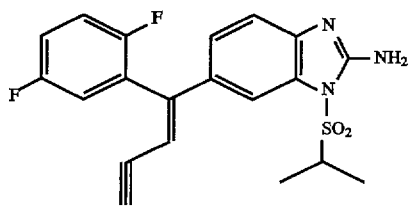

or a pharmaceutically acceptable salt thereof.

29. A method according to claim 25 where the compound is:

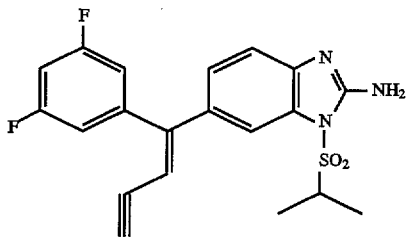

or a pharmaceutically acceptable salt thereof.

30. A method according to claim 25 where the compound is:

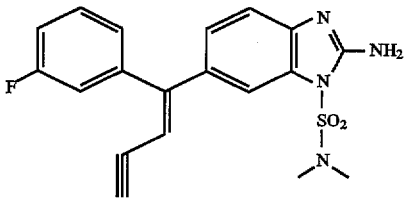

or a pharmaceutically acceptable salt thereof.

31. A method according to claim 21 where the picornavirus is a rhinovirus.

* * * * *

UNITED STATES PATENT AND TRADEMARK OFFICE
CERTIFICATE OF CORRECTION

PATENT NO. : 5,693,661
DATED : December 2, 1997
INVENTOR(S) : Miller, et al.

It is certified that error appears in the above-indentified patent and that said Letters Patent is hereby corrected as shown below:

In column 8, line 42, following "compound", insert --may be further purified, if desired, by common--.

In column 8, line 48, delete "3-bromopropyne, preferably 3-bromopropne," and insert --3-halopropyne, preferably 3-bromopropyne-- therefor.

In column 15, line 29, following "delta", insert --($\delta$)--.

In column 16, first figure, delete

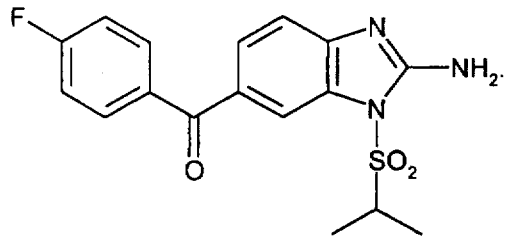

and insert

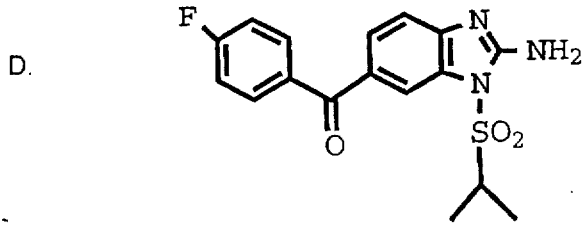

therefor.

In column 16, above the second figure, insert --Preparation 2--.

UNITED STATES PATENT AND TRADEMARK OFFICE
CERTIFICATE OF CORRECTION

PATENT NO. : 5,693,661
DATED : December 2, 1997
INVENTOR(S) : Miller, et al.

It is certified that error appears in the above-indentified patent and that said Letters Patent is hereby corrected as shown below:

In column 17, first figure, delete

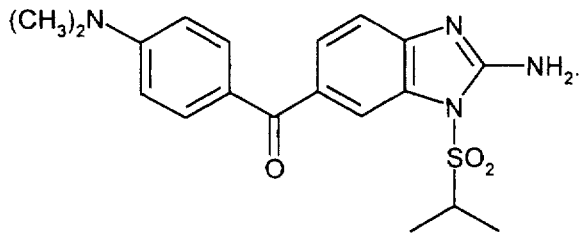
B and insert

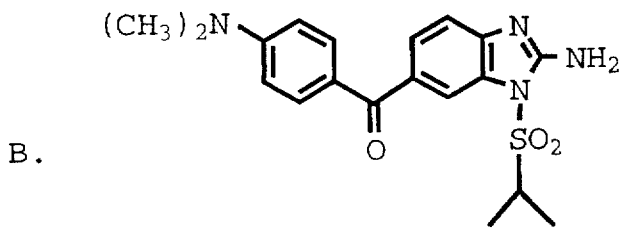
B.

therefor.

In column 17, line 41, delete "1H" and insert --$^1$H-- therefor.

UNITED STATES PATENT AND TRADEMARK OFFICE
CERTIFICATE OF CORRECTION

PATENT NO. : 5,693,661

DATED : December 2, 1997

INVENTOR(S) : Miller, et al.

It is certified that error appears in the above-indentified patent and that said Letters Patent is hereby corrected as shown below:

In column 17, EXAMPLE 1, delete

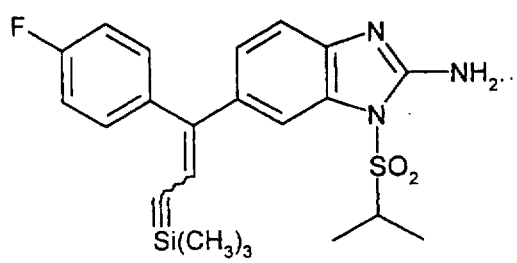

A and insert

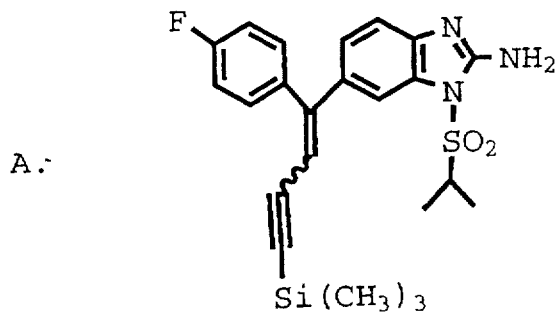

A.

therefor.

UNITED STATES PATENT AND TRADEMARK OFFICE
CERTIFICATE OF CORRECTION

PATENT NO. : 5,693,661
DATED : December 2, 1997
INVENTOR(S) : Miller, et al.

It is certified that error appears in the above-indentified patent and that said Letters Patent is hereby corrected as shown below:

In column 18, first figure, delete

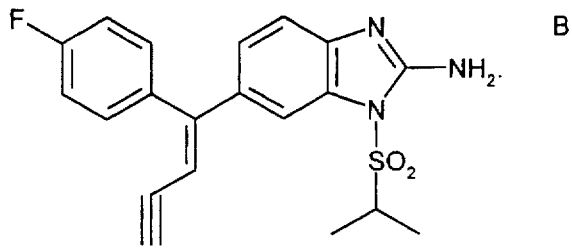

and insert

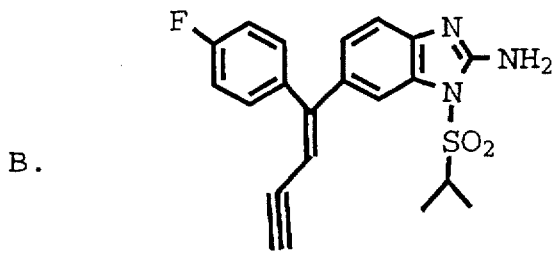

therefor.

UNITED STATES PATENT AND TRADEMARK OFFICE
CERTIFICATE OF CORRECTION

PATENT NO. : 5,693,661
DATED : December 2, 1997
INVENTOR(S) : Miller, et al.

It is certified that error appears in the above-indentified patent and that said Letters Patent is hereby corrected as shown below:

In column 18, second figure, delete

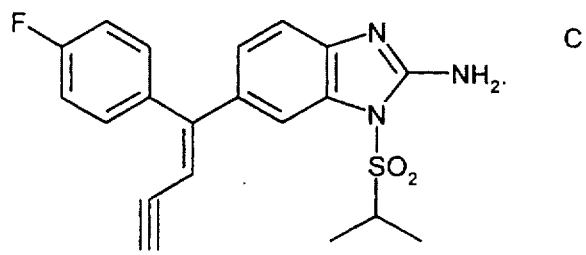

C and insert

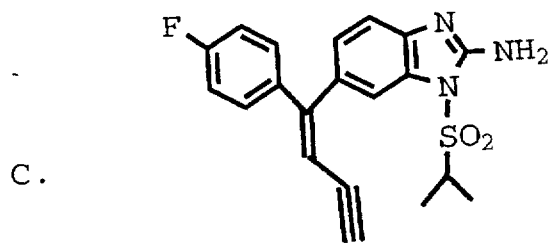

C.

therefor.

UNITED STATES PATENT AND TRADEMARK OFFICE
CERTIFICATE OF CORRECTION

PATENT NO. : 5,693,661
DATED : December 2, 1997
INVENTOR(S) : Miller, et al.

It is certified that error appears in the above-indentified patent and that said Letters Patent is hereby corrected as shown below:

In column 19, EXAMPLE 2, delete

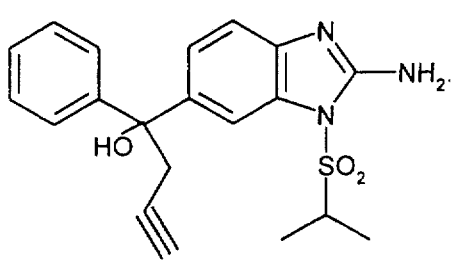

A and insert

A.  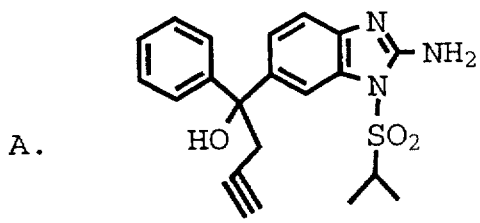

therefor.

UNITED STATES PATENT AND TRADEMARK OFFICE
CERTIFICATE OF CORRECTION

PATENT NO. : 5,693,661

DATED : December 2, 1997

INVENTOR(S) : Miller, et al.

It is certified that error appears in the above-indentified patent and that said Letters Patent is hereby corrected as shown below:

In column 19, second figure, delete

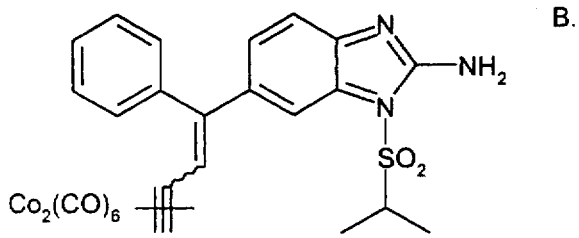

and insert

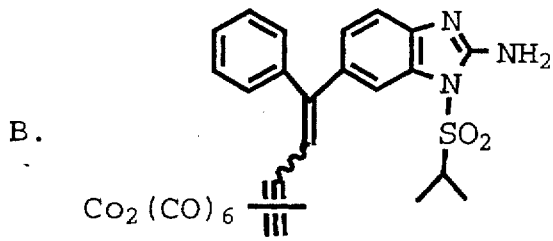

therefor.

UNITED STATES PATENT AND TRADEMARK OFFICE
CERTIFICATE OF CORRECTION

PATENT NO. : 5,693,661
DATED : December 2, 1997
INVENTOR(S) : Miller, et al.

Page 8 of 17

It is certified that error appears in the above-indentified patent and that said Letters Patent is hereby corrected as shown below:

In column 20, first figure, delete

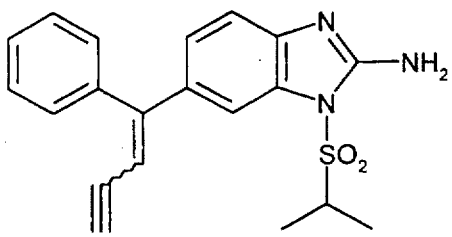   C.

and insert

C.   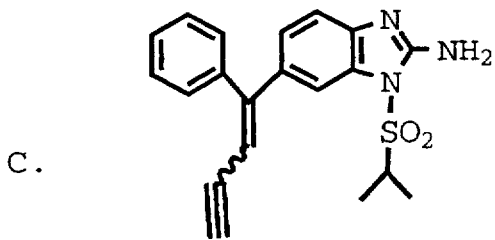

therefor.

UNITED STATES PATENT AND TRADEMARK OFFICE
CERTIFICATE OF CORRECTION

PATENT NO. : 5,693,661
DATED : December 2, 1997
INVENTOR(S) : Miller, et al.

It is certified that error appears in the above-indentified patent and that said Letters Patent is hereby corrected as shown below:

In column 20, line 25, delete "NFLR" and insert --NMR-- therefor.

In column 22, line 31, before "s, 1H);" insert --(--.

In column 22, line 32, after "(s, 1H" insert --)--.

In column 23, EXAMPLE 10, delete

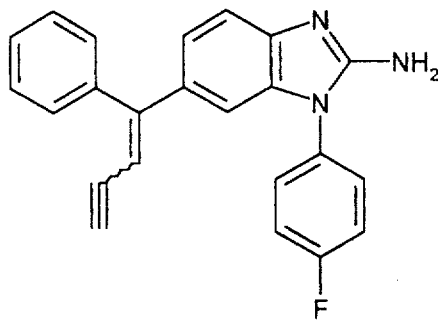

UNITED STATES PATENT AND TRADEMARK OFFICE
CERTIFICATE OF CORRECTION

PATENT NO. : 5,693,661

DATED : December 2, 1997

INVENTOR(S) : Miller, et al.

It is certified that error appears in the above-indentified patent and that said Letters Patent is hereby corrected as shown below:

and insert

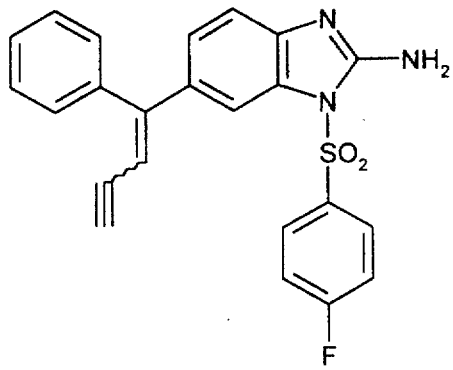

In column 26, EXAMPLE 16, delete

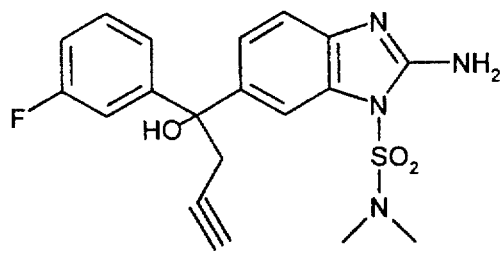

A.

UNITED STATES PATENT AND TRADEMARK OFFICE
CERTIFICATE OF CORRECTION

PATENT NO. : 5,693,661
DATED : December 2, 1997
INVENTOR(S) : Miller, et al.

It is certified that error appears in the above-indentified patent and that said Letters Patent is hereby corrected as shown below:

and insert

A.

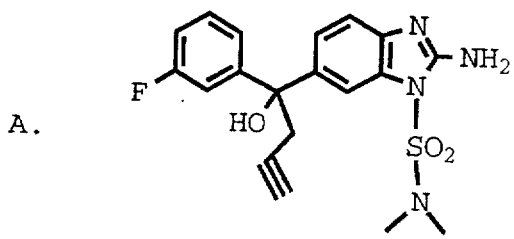

therefor.

In column 26, second figure, delete

B.

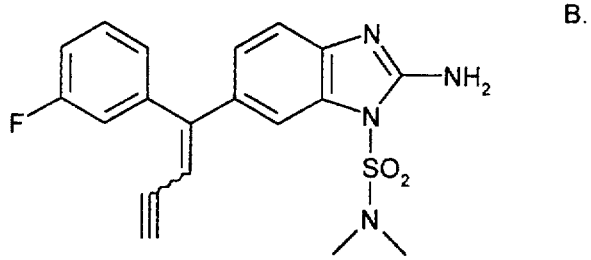

and insert
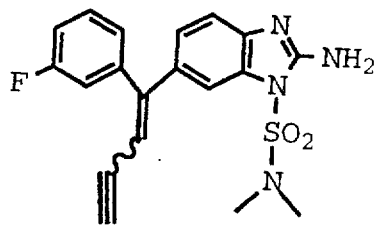
B.
therefor.
In column 27, line 61, delete "RT$_T$" and insert --R$_T$-- therefor.
In column 28, line 56, delete "V$_{max}$" and insert --$\lambda_{max}$-- therefor.
In column 29, line 56, delete "CHC$_{13}$" and insert --CHCl$_3$-- therefor.
In column 31, line 25, delete "V$_{max}$" and insert --$\lambda_{max}$-- therefor.
In column 31, line 39, delete "UV/ViS" and insert --UV/Vis-- therefor.

UNITED STATES PATENT AND TRADEMARK OFFICE
CERTIFICATE OF CORRECTION

PATENT NO. : 5,693,661
DATED : December 2, 1997
INVENTOR(S) : Miller, et al.

It is certified that error appears in the above-indentified patent and that said Letters Patent is hereby corrected as shown below:

In column 33, EXAMPLE 32, delete

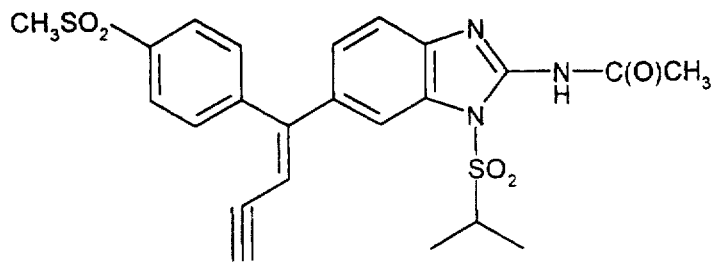

and insert

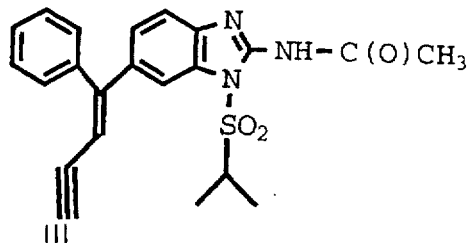

UNITED STATES PATENT AND TRADEMARK OFFICE
CERTIFICATE OF CORRECTION

PATENT NO. : 5,693,661
DATED : December 2, 1997
INVENTOR(S) : Miller, et al.

It is certified that error appears in the above-indentified patent and that said Letters Patent is hereby corrected as shown below:

In column 34, EXAMPLE 33, delete

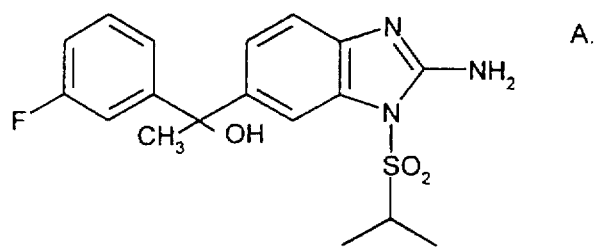

and insert

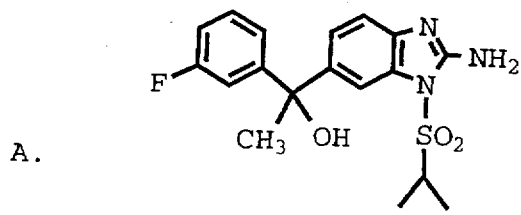

therefor.

UNITED STATES PATENT AND TRADEMARK OFFICE
CERTIFICATE OF CORRECTION

PATENT NO. : 5,693,661

DATED : December 2, 1997

INVENTOR(S) : Miller, et al.

It is certified that error appears in the above-indentified patent and that said Letters Patent is hereby corrected as shown below:

In column 34, second figure, delete

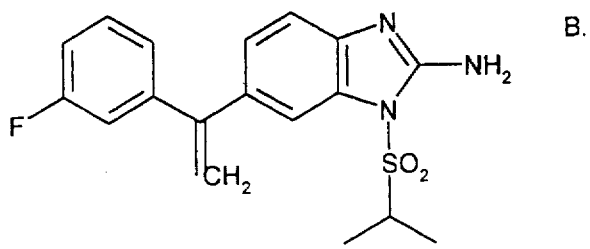

and insert

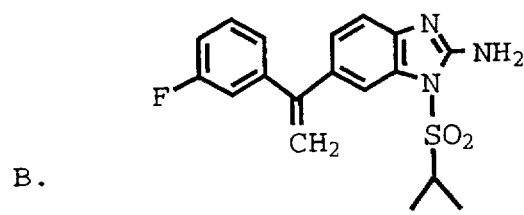

therefor.

In column 34, third figure, delete

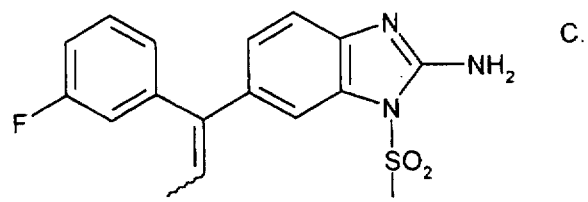

UNITED STATES PATENT AND TRADEMARK OFFICE
CERTIFICATE OF CORRECTION

PATENT NO. : 5,693,661

DATED : December 2, 1997

INVENTOR(S) : Miller, et al.

It is certified that error appears in the above-indentified patent and that said Letters Patent is hereby corrected as shown below:

and insert

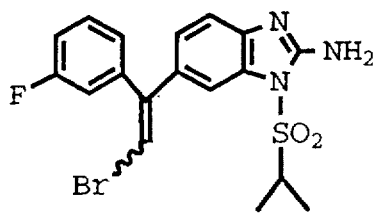

therefor.

In column 35, first figure, delete

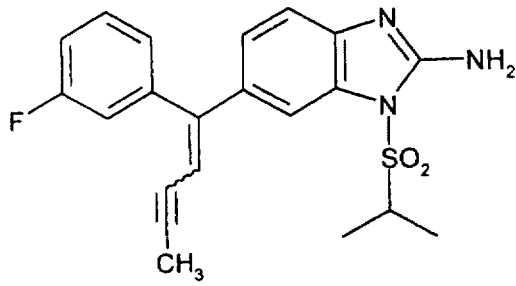

and insert

UNITED STATES PATENT AND TRADEMARK OFFICE
CERTIFICATE OF CORRECTION

PATENT NO. : 5,693,661
DATED : December 2, 1997
INVENTOR(S) : Miller, et al.

It is certified that error appears in the above-indentified patent and that said Letters Patent is hereby corrected as shown below:

D. 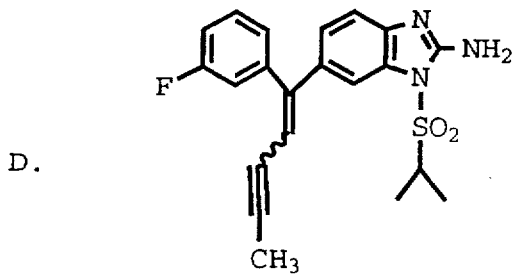

therefor.

In column 44, line 29, delete "3" and insert --$R^3$-- therefor.

In column 46, line 30, delete "haloaen" and insert --halogen-- therefor.

Signed and Sealed this

Twenty-third Day of November, 1999

Attest:

Q. TODD DICKINSON

Attesting Officer    Acting Commissioner of Patents and Trademarks